United States Patent
Plaumann et al.

(10) Patent No.: US 8,979,535 B2
(45) Date of Patent: Mar. 17, 2015

(54) COMPOSITIONS FOR INFILTRATION AND/OR SEALING OF HARD TOOTH TISSUE AND CORRESPONDING METHODS

(71) Applicant: VOCO GmbH, Cuxhaven (DE)

(72) Inventors: Manfred Thomas Plaumann, Cuxhaven (DE); Reinhard Maletz, Cuxhaven (DE); Manfred Stepputtis, Kutenholz (DE); Andree Barg, Otterndorf (DE); Tobias Bloemker, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 0 days.

(21) Appl. No.: 13/645,121

(22) Filed: Oct. 4, 2012

(65) Prior Publication Data

US 2013/0084546 A1   Apr. 4, 2013

(30) Foreign Application Priority Data

Oct. 4, 2011  (EP) .................................... 11183887

(51) Int. Cl.
*A61C 5/00* (2006.01)
*A61C 1/00* (2006.01)
*A61C 3/00* (2006.01)
*A61B 5/00* (2006.01)
*A61K 6/00* (2006.01)

(52) U.S. Cl.
CPC .............. *A61B 5/0088* (2013.01); *A61K 6/0052* (2013.01)
USPC ............................................. 433/215; 433/29

(58) Field of Classification Search
USPC ............... 433/215, 29–31, 226–228.1, 217.1; 523/115–118; 424/9.7, 9.71, 9.8, 424/49–54; 106/35
See application file for complete search history.

(56) References Cited

U.S. PATENT DOCUMENTS

| 4,722,827 | A  | * | 2/1988  | Kwon ........................... 420/422 |
| 4,744,827 | A  |   | 5/1988  | Winkel et al. |
| 6,186,780 | B1 |   | 2/2001  | Hibst et al. |
| 6,254,389 | B1 | * | 7/2001  | Seghatol ....................... 433/215 |
| 6,670,499 | B1 |   | 12/2003 | Inoue et al. |
| 2006/0252845 | A1 | * | 11/2006 | Ruppert et al. ............... 523/115 |
| 2008/0038686 | A1 | * | 2/2008  | Nagai ............................. 433/29 |
| 2010/0016464 | A1 |   | 1/2010  | Craig et al. |

FOREIGN PATENT DOCUMENTS

| EP | 0969789     | 9/2006 |
| WO | 2007028159  | 8/2007 |

* cited by examiner

*Primary Examiner* — Yogesh Patel
(74) *Attorney, Agent, or Firm* — Duane Morris LLP; J. Rodman Steele, Jr.; Gregory M. Lefkowtiz

(57) ABSTRACT

A method for infiltration and/or sealing of hard tooth tissue and for detection of caries in the infiltrated region or under the seal by means of fluorescence, is described. The method includes applying a composition comprising a filler system consisting of or comprising inorganic filler particles surface-modified by means of organic structural elements, wherein the organic structural elements can be reacted with an organic binder system to form covalent bonds, wherein the filler particles of the composition have an average particle size in the range between 1 nm and 150 nm, and an organic binder system comprising one or more polymerizable monomers, wherein the filler system is dispersed in the organic binder system (b). The infiltrated or sealed surface of the hard tooth tissue is then irradiated with excitation radiation which causes emission of fluorescence radiation. The fluorescence radiation data is recorded and used to detect curies.

32 Claims, No Drawings

COMPOSITIONS FOR INFILTRATION AND/OR SEALING OF HARD TOOTH TISSUE AND CORRESPONDING METHODS

CROSS-REFERENCE TO RELATED APPLICATIONS

This application claims priority to European Patent Application No. EP 11 183 887.6, filed Oct. 4, 2011, the entire content of which is incorporated herein by reference.

FIELD OF INVENTION

The present invention relates to compositions which comprise an organic binder system and a filler system dispersed therein. These compositions are used according to the invention in a method for infiltration and/or sealing of hard tooth tissue and for detection of caries in the infiltrated region or under the seal by means of fluorescence and for determination of changes in the state of infiltration or in the seal by means of fluorescence. A further aspect of the present invention relates to a method for recording data of a fluorescence measurement on a tooth, wherein a tooth surface is infiltrated and/or sealed in an appropriate manner. The present invention also relates to a kit comprising a composition according to the invention. Methods of caries therapy and methods of caries diagnostics and for monitoring caries under a sealed tooth surface are also described.

The present invention relates in particular to dental compositions which can be employed as dental sealing material (fissure sealants or sealing material for complete sealing of teeth; also as a photocuring desensitizing lacquer) and thereby allow, for example, the state of activity of initially carious enamel lesions to be determined by means of fluorescence measurement (in particular IR laser fluorescence measurement). The present invention thus relates in particular to compositions which are transparent both to light of the wavelengths required for excitation of the fluorescence on a tooth and to the fluorescence rays emitted after excitation.

BACKGROUND OF THE INVENTION

Caries, which is the most widespread infectious disease in humans, develops in the form of carious lesions when plaque bacteria, primarily mutans streptococci and lactobacilli, form organic acids by an anaerobic metabolism mechanism on fermentable carbohydrates. The acids diffuse into the hard tooth tissue and destroy the crystalline phases of the enamel and dentine. By the dissolving out of these minerals, irreversible structural changes are caused in the hard tooth tissue. This demineralization takes place from a pH of less than 5.5. A continuous precipitation of certain ions, such as calcium and phosphate ions, out of the saliva moreover occurs. The presence of these ions in the oral cavity leads to a remineralization. If fluoride is present, the remineralization is additionally promoted by the formation of acid-resistant fluorohydroxyapatite. In the dynamic medium of the oral cavity, demineralization and remineralization alternate. If an equilibrium exists between these processes, no caries develops. However, if the equilibrium is disturbed, the formation of a carious lesion is promoted by the increasing loss of inorganic constituents of the enamel.

Early detection of caries plays a decisive role in the fight against this disease, since the current state of knowledge is that a progression of caries can be arrested in any stage. If a lesion is detected in the early stage, the probability of successful remineralization is increased significantly. A (minimally) invasive treatment can thus be avoided under certain circumstances.

As a rule, the diagnosis of a carious lesion is made with the aid of a visual/tactile inspection of the particular tooth situation. If it is a matter of occlusal caries, as in most cases, correct diagnosis is an enormous clinical challenge to the dentist, since it is extremely difficult reliably to detect a lesion in fissures and pits even with the aid of a magnifying glass/probe. The difficulty of occlusal caries diagnostics results from the specific morphology of fissures and pits. For this reason alternative diagnostic methods have already been widely developed in the market.

There may be mentioned by way of example at this point methods for detection and for controlled monitoring of changes in the mineralized tissue by optical methods. U.S. Pat. No. 7,796,243 B2 thus proposes the use of optical coherence tomography in combination with Raman spectroscopy. US 2010/0227296 A1 describes methods for evaluation of risk factors with respect to oral health which are based inter alia on physical phenomena, such as luminescence, fluorescence and thermal emissions. US 2007/0021670 A1 relates to apparatuses for detection of caries, demineralization and remineralization which are based on IR photothermal radiometry and luminescence.

Contactless methods and devices which utilize the property of healthy and carious hard tooth tissue to fluoresce naturally have proved to be particularly suitable for detection of caries in particular, but also of plaque, concrements, bacterial attack on teeth etc. By irradiation with high-energy laser light of a particular wavelength, for example, carious regions can be excited to a more intense fluorescence than healthy hard tooth tissue.

DE 30 31 249 C2 describes an investigative method for detection of caries, wherein the tooth is irradiated with virtually monochromatic light. The light beam excites a fluorescence radiation on the tooth. The fluorescence spectrum then emitted by the tooth shows clear differences between carious and healthy regions of the tooth. Thus, in the red spectral region of the fluorescence spectrum of the tooth, between 550 and 650 nm, the intensity is significantly higher than in the case of a healthy tooth, based on incident light of a wavelength of 410 nm. In contrast, in the blue spectral region of the fluorescence spectrum of the tooth, between 350 and 450 nm, the intensity of the fluorescence radiation is almost identical for carious regions and healthy regions of the tooth. It has therefore been proposed to irradiate the tooth with a wavelength of 410 nm and, by means of two filters, to record the fluorescence radiation of the tooth for a first wavelength of 450 nm and a second wavelength of 610 nm, that is to say in the blue and red spectral region, for example with the aid of photodetectors. The fluorescence radiation intensities recorded by this arrangement are subtracted, so that on the basis of the difference in intensity thereby obtained, a healthy region of the tooth can be clearly distinguished from a carious region of the tooth.

An excitation wavelength of 488 nm is stated elsewhere (S. Albin et al., "Laser Induced Fluorescence of Dental Caries", Proc SPIE 907, 96-98, 1988).

DE 42 00 741 C2 reports that a device for detection of caries is equipped with an excitation radiation having a wavelength in the range of from 360 nm to 580 nm and the fluorescence radiation caused on the irradiated tooth in the wavelength range between 620 nm and 720 nm is filtered out. By this measure the separation between the wavelength of the excitation radiation and of the fluorescence radiation emitted is said to be sufficiently wide so that the excitation radiation cannot falsify the results of the evaluation by overlapping the fluorescence radiation.

E. de Josselin de Jong et al. "A new Method for in vivo Quantification of Changes in Initial Enamel Caries with Laser Fluorescence", Caries Research, 2-7, 1995 describes irradiation of the tooth with laser light of a wavelength of 488 nm, recording of the fluorescence radiation of the tooth for wavelengths from 520 nm via a CCD camera and mathematical evaluation of the data, in order to be able to detect a carious tooth region in this way.

DE 93 17 984 U1 discloses a device for detection of caries, wherein the excitation radiation is generated not continuously but in pulsed form during an excitation interval.

U.S. Pat. No. 7,596,253 discloses methods and devices for detection of caries, wherein fluorescence image data are generated and processed.

DE 297 04 185 U1 proposes a device for detection of caries, with which a tooth to be investigated is irradiated homogeneously and the excited fluorescence spectrum of the tooth is said to be recorded more accurately. The emission and recording equipment of this device has a plurality of individual emission fibres and detection fibres which can be arranged in alternation relative to one another. In particular, an emission fibre is said to be surrounded coaxially by several detection fibres.

DE 195 41 686 B4 describes a device for detection of caries, plaque or bacterial attack on teeth which is said to have improved properties. The wavelength of the excitation radiation generated by a light source here is between 600 nm and 670 nm.

DE 198 25 021 A1 describes methods and devices for detection of caries, plaque or bacterial attack on teeth, wherein the fluorescence radiation is evaluated with wavelengths above approx. 800 nm. A particularly sensitive recording of hidden caries, such as in fissures or in the approximal tooth region, is said to be achievable with this measure, since in this wavelength region the proportion of caries-specific fluorophores and other deposits is particularly high, but healthy tooth enamel or dentine gives out no or only little fluorescence.

Further methods and/or devices for detection of bacterial attack on teeth which are based on optical principles are to be found in the publications DE 197 09 500 C1, DE 202 09 441 U1, DE 102 27 128 A1, DE 603 16 699 T2, DE 196 19 067, DE 10 2005 052 294 A1, DE 94 17 470 U1 and DE 101 33 451 A1.

The now technically widely developed methods of diagnosis for early detection of caries must of course be accompanied by suitable therapeutic methods which have the effect that the caries attack does not progress further and stops, as far as possible avoiding an invasive intervention by the dentist. In this respect, sealing of teeth (in particular sealing of fissures and pits, but also in the sense of complete sealing of the tooth) with mechanically highly resistant, retention-secure, abrasion-resistant and readily flowable plastics compositions has proved to be appropriate.

"Sealing of fissures and pits" (also summarized as "sealing of fissures" in the following) is understood as meaning filling of the sometimes very deep pits, rough furrows and grooves on the surface of teeth with a readily flowing plastics material. The often narrow indentations on the chewing surfaces of a tooth are called fissures. In children and adolescents, but also in adults, caries often develops first in the fissures of the chewing surfaces, the occlusal surfaces of the lateral teeth displaying the highest susceptibility to caries. A highly developed and fissured relief is also to be found, for example, on the inside of the front teeth, so that here also sealing for prophylaxis of caries may be appropriate. In addition, a clearly pronounced fissure relief also promotes adhesion of plaque. Accumulation of plaque has also been observed in narrow fissures and on steeply sloped protuberances.

The various types of fissure (for example ampoule-shaped, I-shaped, U-shaped, V-shaped) can accommodate residues of food and therefore also offer an ideal and protected habitat for caries-causing bacteria, since oral hygiene measures, such as brushing teeth, do not reach here. The bristles of toothbrushes are in general too wide to be able to clean the base of the fissure. The morphology of the fissures therefore makes mechanical cleaning of the pits almost impossible. If an enamel caries were to arise in the fissure, it will highly probably spread very rapidly into the dentine, since the thickness of the enamel in the region of the fissure, especially at the base of the fissure, as a rule is very thin. The high susceptibility of fissures to carious attack is therefore chiefly explained by their specific morphology.

The risk of caries in fissures is also increased significantly compared with smooth tooth surfaces if a fluoride prophylaxis is performed, since a fluoride prophylaxis cannot display the accustomed efficacy in the fissures.

By sealing the fissures, the relief of the tooth is flatter, the tooth is easier to clean and the development of caries can be prevented in this way. Sealing of fissures is nowadays acknowledged as a proven and recommended, effective prophylactic measure and is used ever more widely in daily dental practice. The rule is that all fissures and pits at risk from caries should already be sealed as a precaution. It has been possible to demonstrate that such a procedure leads to a significant decrease in cariogenic microorganisms in the fissure underneath the seal.

DETAILED DESCRIPTION OF THE INVENTION

As already stated above, the present invention relates in particular to compositions for use in a method for infiltration and/or sealing of hard tooth tissue (healthy or carious) and in a method for detection of caries under the seal by means of fluorescence and in a method for determination of changes in the state of infiltration or in a seal by means of fluorescence. In this context, the hard tooth tissue can be healthy or carious. In this context, the present invention still relates to a method which consists of at least two method steps. The first method step is the method for infiltration and/or sealing of hard tooth tissue. After the hard tooth tissue has been infiltrated and/or sealed, the second method step is then carried out. The second method step is the method for detection of caries under the seal by means of fluorescence. A third method step, which is the method for determination of changes in the state of infiltration or in a seal by means of fluorescence, can optionally also be carried out.

The infiltration of carious hard tooth tissue can be, in particular, an infiltration of an initial carious lesion, this being areas of tooth enamel of increased pore volume. These pores represent diffusion pathways for progressive breakdown of the tooth enamel structure, for which reason it has already been proposed to achieve both a closure of the diffusion pathways and a stabilizing of the damaged enamel structure by infiltration with curable materials. It has been demonstrated that plastics compositions of low viscosity infiltrate (penetrate) into carious lesions, and after curing can prevent a further demineralization of the tooth enamel.

In one method for infiltration of healthy hard tooth tissue, hard tooth tissue is infiltrated (for example there where it is not protected by a layer of tooth enamel due to receding of the gum or due to breakdown of tooth enamel) using a low-viscosity plastics material in that the plastics material penetrates into the hard tooth tissue.

In one method for sealing hard tooth tissue, infiltration of the hard tooth tissue may occur at the same time. In the context of the present text, "sealed hard tooth tissue" is understood as meaning a hard tooth tissue on the surface of which is formed a cured layer of a plastics material (sealing material). In dental practice, fissures and pits of a tooth are sealed in particular. In isolated cases, however, "complete sealing" of teeth is carried out in order to achieve an improved prophylactic action. In the context of complete sealing, however, it has so far proved to be a disadvantage that the sealing materials employed adhere only inadequately to smooth tooth surfaces.

The adhesion of conventional sealing materials to tooth surfaces in the region of fissures and pits is also regarded as not yet adequate; this applies in particular with respect to transparent sealing materials which render possible the detection of caries under the seal by means of fluorescence.

In dental practice, compositions which comprise an organic binder system based on dimethacrylate are conventionally employed as sealing materials. these sealing materials either have no filler content or have a lower filler content compared with filling composites. Such sealing materials having no or only a low filler content show the most favourable retention properties in dental practice. Because of their low viscosity, such sealing materials penetrate better into the depth of a fissure or into pores of a lesion or the tubuli of exposed dentine compared with filling composites. However, it is a disadvantage that because of the lower filler content such sealing materials are less abrasion- and flexing-resistant than conventional dental filling materials.

A distinction is made between sealing materials in practice, for example, according to the nature of their curing, which can be carried out by photo- and/or autopolymerization. Photocurable sealing materials which are present in the form of one-component materials are less susceptible during processing compared with two-component autopolymerizable sealing materials since there can be no bubble formation during mixing. Photocurable sealing materials are therefore conventionally preferred. In addition to photocurable and two-component autopolymerizable sealing materials, so-called dual-curing systems which can be cured by photocuring and chemical curing are also known.

A further distinguishing criterion for distinguishing between sealing materials relates to their appearance. A distinction is thus made between transparent and coloured products. Transparent sealing materials either have no filler content (i.e. they comprise no filler system comprising filler particles) or have nanoscale filler particles added to them, the size of which is smaller than the wavelength of visible light. Transparent sealing materials allow the dentist, for example after sealing a fissure, to detect a possible development or progression of caries in the depth of the fissure.

Many variants of dental sealing materials are also available as fluoride-releasing materials.

DE 23 01 067 proposes dental fissure sealing agents which are said to have greatly improved handling properties and an outstanding capacity for completely filling and sealing developing holes and fissures in teeth, their compositions comprising as the main curable monomer component glycol dimethacrylates, such as, for example, ethylene glycol dimethacrylate, diethylene glycol dimethacrylate etc. It is explained that the use of aromatic dimethacrylates is unsuitable for sealing fissures since their viscosity is said to be too high for them to flow into the holes and fissure and complete sealing and good adhesion is said to be non-achievable with them. The compositions described are two-component in configuration and are cured by chemical means.

It is to be expected that compositions such as are described in DE 23 01 067 will take up a large amount of water because of the relatively large amount of reactive monomer component. The ether groups —$CH_2$—$CH_2$—O— present in the monomer display free, unimpeded rotation and form highly flexible molecular chains. The packing of the chains in the polymer is therefore not rigid and fixed, but mobile. As a result, the polymeric network is opened for entry of water. If large amounts of water enter into the polymer, this is additionally expanded and will be split and broken down irreversibly by hydrolysis.

U.S. Pat. No. 6,573,312 B2 describes a composition for sealing/filling fissures and pits which comprises a chemically modified Bis-GMA (2,2-bis[4-(2-hydroxy-3-methacryloyloxypropoxy)phenyl)propane). The composition is said to achieve improved physical and mechanical properties of the polymer, and the polymerization reaction is said to be carried out at higher rates by photocuring. The Bis-GMA is modified by successive reaction of the secondary hydroxyl groups of the Bis-GMA with methacrylic acid chloride in the presence of an organic amine. In the first synthesis step, the dimethacrylate is thus reacted to give a trimethacrylate (Tri-GMA), which is reacted in a second step to give a tetrafunctionalized methacrylate (Tetra-GMA). The compositions consist of Bis-GMA and Tri-GMA and of Bis-GMA, Tri-GMA and Tetra-GMA, the compositions furthermore comprising fillers, photoinitiators, additives and diluting monomers. Methyl methacrylate and glycol dimethacrylate are proposed as diluting monomers.

The particular properties of dental compositions based on Bis-GMA are based on the possibility of the molecule forming via hydrogen bridge bonds, starting from the free hydroxyl groups, additional structural units, so-called superstructures or secondary/tertiary structures, alongside the linking via the methacrylate groups. The build-up of such superstructures can likewise be promoted by carbamate, amide or similarly composed groups, but not by ester groups. Furthermore, due to the rigid conformation of the bisphenol A structural motif, the polymer has close, densely packed molecular associations which interact with one another via several types of bond. These structural prerequisites are the reason for the good mechanical and physical properties of Bis-GMA polymers.

If these additional interactions are blocked by functionalization of the free hydroxyl groups, as is the case according to U.S. Pat. No. 6,573,312 B2, the formation of the superstructures should be impeded and a decrease in the physical and mechanical values of the cured components should be the consequence. The values of the physical properties listed in U.S. Pat. No. 6,573,312 B2 are merely estimated. Relevant differences between the values of the comparative examples and those of the examples according to the invention according to U.S. Pat. No. 6,573,312 B2 are not to be seen.

US 2005/0288387 A1 describes dental compositions which are said to be employable for coating teeth or as dental sealing materials. The compositions comprise a multiacrylate compound, an initiator and an alcohol. The multiacrylate compound comprises at least 3 acrylate units per molecule, for example dipentaerythritol pentaacrylate, di-trimethylolpropane tetraacrylate, trimethylolpropane triacrylate etc. The initiator is preferably a photoinitiator.

US 2009/0047633 A1 relates to a dental sealing and/or coating system which adheres to hard tooth tissue itself. The composition comprises 10 to 60 wt. % of a polymerizable compound, comprising Bis-GMA and urethane compounds or mixtures thereof, 1 to 40 wt. % of a polymerizable acid compound, 3 to 60 wt. % of a silica filler having an average particle size of from 1 to 100 nm, 1 to 30 wt. % of water and 10 to 60 wt. % of solvent.

EP 0 969 789 B1 describes dental sealing and coating materials which comprise at least 10 wt. % of a polymerizable material, 0.01 to 20 wt. % of a filler in the nano range which has a primary particle size of between 1 and 100 nm, the surface of the filler in the nano range being modified by a chemical surface treatment with a silanizing agent, and at least 10 wt. % of an organic solvent having a boiling point below that of water.

U.S. Pat. No. 6,899,948 B2 discloses dental sealing materials comprising non-aggregated, surface-modified silica particles having average particle sizes of less than 200 nm, alongside curable monomers.

U.S. Pat. No. 6,572,693 B1 discloses dental materials which can also be employed for sealing. Alongside a curable resin matrix, these compositions comprise clusters of nanoscale particles and non-agglomerated nanoscale particles. The nanoscale particles can be silica particles, while the clusters comprise heavy metal oxides in order to ensure the radio-opacity of the material.

WO 2007/028159 A2 relates to clear, transparent and opaque dental sealing compositions in which colloidal silica particles having an average particle size of from 10 to 100 nm are dispersed in methacrylate(acrylate) resin. The compositions are photochemically curable and are said to give hard, smooth and glossy coatings on the tooth. The non-agglomerated silica particles are said to be distributed homogeneously within the resin matrix, so that the dispersion has a low viscosity. The content of silica in the dispersion is up to 60 wt. %. The polymers are said to have good mechanical values, such as abrasion resistance. Preferably, the compositions are used for sealing fissures and pits on the surface of a tooth or a restoration.

WO 01/30307 A1 discloses dental compositions having a visual opacity at a value of less than 0.25. Since the reciprocal property of translucency is opacity, a composition having translucency values which are greater than 0.75 is described here. These compositions contain silica particles having an average diameter of less than 200 nm, alongside a curable resin composition.

A temporary, transparent, dental lacquer composition for coating tooth surfaces is disclosed in US 2006/0063853 A1. Transparency is effected here by the addition of hollow glass beads to the composition. In order to bring about this effect, the refractive index of the binder must be lower than that of the hollow glass beads.

Both US 2007/0166450 A1 and US 2010/0016464 A1 describe dental coating and sealing materials which comprise fluorescence agents.

U.S. Pat. No. 6,670,499 B1 discloses compositions which can be employed for sealing teeth. Some of the monomers employed in U.S. Pat. No. 6,670,499 B1 have structural units which are adamantane derivatives.

WO 2005/094757 A1 discloses a dental composition which is suitable for use as a fissure and pit sealant and comprises a polymerization system which can be cured by means of heat and is subject to a step-growth polymerization.

EP 1 307 173 B1 discloses a fluoride lacquer and fissure sealing material based on silicone.

The publications DE 20 2006 020 483 U1, DE 20 2006 020 480 U1, DE 20 2006 020 479 U1, DE 20 2006 020 477 U1, DE 20 2006 020 476 U1, EP 2 023 884 A1, EP 1 854 445 A1, EP 2 145 613 A1 and EP 2 151 229 A2 relate to compositions for infiltration of tooth enamel in the treatment or prevention of caries lesions.

Nanoscale particles in dental compositions, which nevertheless are not envisaged for sealing teeth, are furthermore described in U.S. Pat. No. 5,936,006 A, U.S. Pat. No. 6,194,481 and U.S. Pat. No. 6,593,395 B2.

In "Effects of composite fissure sealants on IR laser fluorescence measurements", Lasers Med Sci, 23, 133-139, 2008 the concept of sealing of enamel as a therapeutic measure for arresting caries attack was combined with that of a fluorescence-based optical method of caries diagnostics. The results of the study showed that it is possible for the caries activity under sealing materials which have no filler content or are transparent and have a filler content of nanoscale particles to be monitored clinically in a reliable manner.

Nanoscale, highly disperse filler particles are normally distinguished in that the particles are present in isolated form in the resin matrix in the form of a suspension. In this context, the particles essentially display neither aggregation nor agglomeration. A nanoscale particle is thus normally present in a discrete form and is a particle detectable as an individual by suitable physical methods (for example by transmission electron microscopy). The diameter of a nanoscale particle and therefore its size is less than 200 nm, preferably less than 150 nm. Particle sizes of from 1 nm to 100 nm are particularly preferred also for the present invention.

The term "aggregate" is understood as meaning a fixed assembly of primary particles into secondary or tertiary particles etc. The term "agglomerate" is understood as meaning a non-fixed assembly of "aggregates". A breaking up and a division of "agglomerates" into the "aggregates" on which they are based is comparatively easily possible by introduction of mechanical energy into the suspension, for example by dispersion. A further breakdown into the individual primary particles is then no longer readily possible.

Examples of highly disperse, nanoscale fillers which are present in the discrete form are amorphous silicas. The (primary) particles in general have diameters of from 1 nm to 150 nm and are as a rule spherical. The inside of the individual particles conventionally consists of a framework of siloxane compounds which results from the linking of $[SiO_4]$ tetrahedra or of polysilicas. The particles can be present dispersed in a liquid as a silica sol. The silica is then called colloidal silica.

Such substances can be prepared in various ways.

For example, they can be synthesized by means of flame hydrolysis of chlorosilanes. Specific pyrogenic silicas are obtained in this preparation process. Pyrogenic silicas can acquire different primary particle sizes, depending on the synthesis conditions, the aggregation of the primary particles increasing with decreasing primary particle size. Thus, for example, the pyrogenic silica AEROSIL OX 50, as the coarsest commercially obtainable silica having a particle diameter of 40 nm which is prepared by the flame hydrolysis process, is present largely as isolated particles of spherical shape. With respect to its "non-aggregated" and "non-agglomerated" structure, the manufacturer equates it structurally with the silicas which originate from the wet chemistry "sol-gel process" (see Degussa, Schriftenreihe Pigmente, Zur Bedeutung und Existenz von Primärteilchen bei hochdispersen Stoffen, number 60, page 10-11) When the primary particle size decreases, the tendency of pyrogenic silicas to assemble into aggregates increases.

Highly disperse, nanoscale fillers which are present in discrete form, that is to say as isolated, individual particles, can also be prepared by means of the "sol-gel" process. Silicas are built up by here by controlled hydrolysis and condensation.

Starting from sol-gel precursors, such as metal alkoxides, for example tetraalkoxysilane, a hydrolysis and condensation are carried out, for example, in alcohol or water under basic catalysis. This reaction can also proceed under acid catalysis. On the basis of the large number of influencing parameters (catalyst, molar ratio, temperature, time, pH, reaction medium etc.) in this wet chemistry process, desired property parameters can be controlled in a targeted manner. The presence of hydroxyl groups on the surfaces of the particles in combination with the acid or basic character of the suspension render possible the adjustment of the stability of a particle dispersion over a broad pH range on the basis of interparticular electrostatic repulsion. Narrow particle size distributions result here. The preparation process explained above is also called "Stöber synthesis".

With sol-gel processes, the preparation of nanoscale metal and heavy metal oxides and of mixed oxides is also possible.

According to a preferred alternative process for the preparation of colloidal silica sol, water-glass is used as the starting substance. In this process, an aqueous solution of sodium silicate is deionized by means of an ion exchanger, as a result of which silica is formed. This acid is unstable and polymerizes to give small particles, from which the nanoscale silicas are then formed. By suitable adjustment of the process parameters, narrow particle size distributions can also be obtained here.

The inorganic filler particles of dental compositions are often surface-treated organically. An organic surface treatment conventionally improves the compatibility of the particle surface with the organic binder phase, since the particle surface which is hydrophilic per se is hydrophobized by the surface treatment and then has a better compatibility with the plastics matrix. The surface modification is preferably carried out such that during curing of the material, by copolymerization, the inorganic surface is covalently bonded into the polymer formed. The inorganic surface is often silanized. In this procedure, prehydrolysed methacryloxyalkyltrialkoxysilanes, such as, for example, 3-methacryloxypropyl-trimethoxysilane, in which the silanol groups formed during the hydrolysis react with the free hydroxyl groups of the filler surface are employed. Information on modification reagents and methods of implementation are known, inter alia, from DE 24 05 578 A1, US 2002/0065337, DE 195 08 586 A1, WO 00/69392 and U.S. Pat. No. 6,387,981. Such processes for modification of the surface of the inorganic particles are also preferred in the context of the present invention (see below).

Like the pyrogenic silicas prepared by flame hydrolysis, which are obtainable commercially in various particle sizes through the "Aerosils" (Degussa) or "CAB-O-SIL" (Cabot Corporation) product series, the silicas prepared by alternative processes can also arise commercially in various sizes through the "Highlink" (Clariant), "Nalco" (Nalco Chemical Company), "Nanocryl" (Nanoresins), "Bidzil" (Eka Chemicals), "Levasil" (H.C. Starck), "NexSil" (Nyacol) or "Ludox" (du Pont) product series.

For suitable silica sols, reference may also be made to DE 600 12 775 T2, DE 10 2006 044 520 A1, EP 2 110 414 A1 and the references cited there.

A primary object of the present invention was to provide a composition for use in a method for infiltration and/or sealing of hard tooth tissue and for subsequent detection of caries in the infiltrated region or under the seal by means of fluorescence. The hard tooth tissue to be infiltrated or sealed in this context should be either carious or healthy.

In order to render possible detection of caries in the infiltrated region or under the seal by means of fluorescence, the composition should preferably be configured such that it can be cured to give a sealing material which has a high transmission (preferably >70% transmission at a layer thickness of 1 mm) in the wavelength range required for the detection.

In this context, the composition to be provided should preferably simultaneously have an outstanding adhesion to and retention on the tooth enamel in the cured form, and in this context also preferably at the same time have outstanding mechanical properties (even after ageing), in particular the flexural strength and the abrasion resistance should be particularly high.

Furthermore, the composition to be provided should place the treating dentist in the position of carrying out measurements on the sealed or infiltrated tooth such that he obtains as much information as possible on the state of health of the treated tooth (in particular on the presence or absence of caries) and on the quality or the properties which change with respect to time of the seal applied or of the state of infiltration.

The composition to be provided should preferably also render possible a monitoring of the sealed or infiltrated tooth and of an applied seal over a relatively long period of time, and put the treating dentist e.g. in the position to determine a suitable point in time for the removal of a seal which no longer adequately fulfils its purpose as precisely as possible and in a simple manner.

According to a closely related aspect, it was a corresponding object of the present invention to provide an improved method for recording data of a measurement on a sealed or infiltrated tooth surface of a tooth.

It was a further closely related object of the present invention to provide an improved method for preparation for caries diagnostics on a tooth of a patient. A corresponding method for caries diagnostics should in this context be linked to the preparation method to be provided according to the invention.

In connection with the (part) objects described above, on which the present invention is based, it is to be pointed out that as described above with reference to the state of the art, a plurality of compositions which are suitable for infiltration and/or sealing of tooth surfaces (in particular fissures and pits, but also, for example, exposed dentine, in this context see above) are indeed known, but however quite generally the search for a suitable sealing material is associated with particular difficulties if the material to be provided not only is to render possible a brief sealing, but at the same time is to meet a number of further requirements.

Summarizing, some of the requirements of a composition to be provided which are mentioned above are the following:
  good retention on the tooth enamel or a good adhesion by penetration into the dentine tubuli, even after ageing,
  further good mechanical properties (in particular flexural strength and abrasion resistance),
  high transmission in the wavelength range used for caries diagnostics,
  a sealed tooth surface can be investigated through the sealing material applied and cured, without destroying the sealing material,
  the quality and the properties of the seal applied to a tooth surface which change with time can be readily checked, also in the context of monitoring over long periods of time, without destroying the sealing material; the state of infiltration can correspondingly be readily checked,
  in the cured state, the composition should have a water uptake of less than 25 µg/mm$^3$,
  the composition should have good flow properties.

In this context, the properties of the material to be found should be measured under measurement conditions such as are described below in the "Methods for determination".

Surprisingly, it has emerged in our own investigations that all of the abovementioned (part) objects can be achieved by using a composition comprising
(a) a filler system consisting of or comprising inorganic filler particles surface-modified by means of organic structural elements, wherein the organic structural elements can be reacted with an organic binder system to form covalent bonds,
   wherein the filler particles of the composition have an average particle size in the range between 1 nm and 150 nm,
(b) an organic binder system comprising one or more polymerizable monomers,
wherein the filler system is dispersed in the organic binder system (b).

The composition according to the invention is preferably configured such that the one monomer or one, several or all of the several polymerizable monomers of the organic binder system (b) comprises at least one structural element Z which independently of any further structural elements Z is chosen from the group consisting of

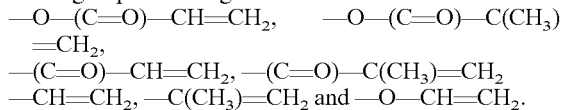

—(C=O)—CH=CH$_2$, —(C=O)—C(CH$_3$)=CH$_2$ —CH=CH$_2$, —C(CH$_3$)=CH$_2$ and —O—CH=CH$_2$.

The average particle size is determined in this context for the total content of filler particles in the composition. If various types of filler particles are present in the composition, alongside surface-modified, inorganic for example organic or non-surface-modified filler particles, all of these filler particles are thus taken into account in the determination of the average particle size. See below for the method for determination of the average particle size.

By varying the constituents and ratios of amounts of the binder system and filler system, the physical properties of a composition according to the invention and of the bodies (in particular layers) originating therefrom by curing can be controlled individually. Starting from the information given above and below, and in particular taking into account the following examples, the person skilled in the art will arrive at compositions according to the invention which meet the requirements of the particular individual case with the aid of simple systematic investigations.

Preferably, the filler system consists of inorganic filler particles surface-modified by means of organic structural elements, wherein the organic structural elements can be reacted with the monomers to form covalent bonds, The inorganic filler particles which form the filler system or which it comprises preferably have a specific surface area, before the surface modification (for this, see below), of >380 m$^2$/g, preferably >450 m$^2$/g, measured by the BET method. For the method for determination chosen, see below.

Such a composition is suitable and intended according to the invention for use in a method for infiltration and/or sealing of hard tooth tissue and for detection of caries in the infiltrated region or under the seal by means of fluorescence. In this method, the method step for infiltration and/or sealing of hard tooth tissue is always first carried out, and the method step for detection of caries in the infiltrated region or under the seal by means of fluorescence is always then carried out. According to the invention, a composition is therefore suitable and intended for use in a method for detection of caries in the infiltrated region of hard tooth tissue or under the seal of hard tooth tissue by means of fluorescence.

In this context, the hard tooth tissue can be carious or healthy. Preferably, such a composition is intended for use according to the invention in a therapeutic dental method as a sealing material for sealing fissures and/or pits and/or carious lesions.

In view of the intended use mentioned, it goes without saying that the composition provided according to the invention is both transparent to fluorescence light which is emitted after appropriate excitation of the healthy or carious hard tooth tissue and transparent to light which is suitable for excitation of a corresponding fluorescence. The composition according to the invention is preferably transparent to light in the wavelength region of >400 nm.

Preferably, the composition according to the invention overall is intended for use in methods which comprise the following measures: (a) infiltration and/or sealing of hard tooth tissue, (b) subsequent detection of caries in the infiltrated region or under the seal by means of fluorescence and/or (c) determination of changes in the seal by means of fluorescence. Measure (a) is always carried out in combination with measure (b) and/or (c).

Without the knowledge that it is suitable for fluorescence investigations in the cured state, the (transparent) composition according to the invention could not be used without limitation for the purpose of infiltration and/or sealing of hard tooth tissue, since the treating dentist cannot determine the quality of the infiltration or of the seal with adequate reliability without the fluorescence technique. Only by the combination of the composition with the use of fluorescence techniques is he placed in a position to monitor the quality and to discover a suitable point in time for supplementary prophylactic measures.

The compositions to be used according to the invention preferably comprise inorganic filler particles which have been surface-modified by means of organic structural elements and have not been prepared by flame hydrolysis, preferably in a content of from 50 to 100 wt. %, based on the total weight of filler particles employed in the composition according to the invention. These filler particles result from the reaction of inorganic filler particles which have not been prepared by flame hydrolysis with suitable agents for surface modification, conventionally from the reaction of such filler particles with suitable agents containing alkoxysilane groups. Such preferred compositions according to the invention surprisingly have outstanding retention properties on hard tooth tissue and further outstanding mechanical properties, such as, in particular, a particularly high flexural strength and abrasion resistance. They largely retain these properties even after ageing. In our own investigations, such preferred compositions according to the invention have been found to be superior compared with compositions which predominantly or exclusively comprise filler particles prepared by flame hydrolysis. In our own investigations (for these, see the examples below), compositions which comprise filler particles based on silica were compared in particular. The person skilled in the art will take this knowledge into account if he intends to formulate further compositions with the properties sought in the context of the present invention starting from the following examples below.

The composition according to the invention is preferably configured such that it can be cured to give a sealing material which has an adhesion to tooth enamel of more than 15 MPa, preferably more than 17 MPa.

The composition according to the invention is preferably configured such that it can be cured to give a sealing material which has flexural strength of more than 80 MPa, preferably more than 90 MPa, particularly preferably more than 100 MPa.

In this context, the composition according to the invention is configured (preferably at the same time) such that it can be cured to give a sealing material which has an abrasion, determined by the ACTA 3 media abrasion method (see below for the method for determination), of less than 80 µm, preferably less than 70 µm, particularly preferably less than 60 µm.

Particularly preferably, the composition according to the invention is configured such that it can be cured to give a sealing material which has both the flexural strength mentioned and the abrasion mentioned.

A particularly preferred composition according to the invention is configured such that it can be cured to give a sealing material which, at a layer thickness of 1 mm, has a transmission of 70% or more, preferably of 75% or more, particularly preferably of 80% or more for perpendicularly incident radiation having a wavelength of 700 nm. 700 nm is a wavelength such as is present in the fluorescence spectrum which arises in the fluorescence of carious and healthy hard tooth tissue, the fluorescence intensity for carious hard tooth tissue being significantly greater at this wavelength than for healthy hard tooth tissue.

Preferably, the composition according to the invention is additionally configured such that it can be cured to give a sealing material which, at a layer thickness of 1 mm, has a transmission of 70% or more, preferably of 75% or more, particularly preferably of 80% or more for perpendicularly incident radiation having a wavelength of 655 nm. The wavelength of 655 nm is a preferred excitation wavelength for fluorescence investigations on the tooth.

Very particularly preferably, the composition according to the invention is configured such that it can be cured to give a sealing material which, at a layer thickness of 1 mm, has a transmission of 70% or more, preferably of 75% or more, particularly preferably of 80 or more for perpendicularly incident radiation, wherein
(a) the transmission is determined in the entire wavelength spectrum of visual light, preferably with a spectrocolorimeter (ColorFlex) from HunterLab (for this, see the explanations below), and/or
(b) the transmission is determined at a wavelength of 500 nm, preferably with a UV/VIS spectrometer, preferably of the Lambda 650 type (PerkinElmer) (for this, see the explanations below).

Preferably, the composition according to the invention is additionally characterized in that the contact angle of the composition on dry tooth enamel, measured with a contact angle meter from Krüss (DSA 100), is less than 60°, preferably less than 50°, particularly preferably less than 40°.

Preferably, the composition according to the invention is configured such that it can be cured to give a sealing material of which the water uptake is less than 15 µg/mm$^3$ preferably less than 13 µg/mm$^3$, particularly preferably less than 10 µg/mm$^3$.

Particularly preferably, the composition according to the invention is configured both such that it can be cured to give a sealing material which has not only the transmission mentioned, and also at the same time also (i) the flexural strength mentioned and/or (ii) the abrasion mentioned and/or (iii) the contact angle mentioned for the composition on dry tooth enamel and/or (iv) the water uptake mentioned.

Both surface-modified silica particles prepared by flame hydrolysis and surface-modified silica particles which have not been prepared by flame hydrolysis, which can lead to easily distinguishable properties of the compositions to be employed according to the invention, can be employed according to the invention. Since both surface-modified silica particles prepared by flame hydrolysis and surface-modified silica particles prepared by flame hydrolysis can be present in a largely non-aggregated and non-agglomerated form, the reason for the different properties of the particular compositions can be only presumed. Two reasons, based on the difference in the preparation process of the particles, possibly play a decisive role:

Thus, on the one hand it is known that the number of free hydroxyl groups in silica particles prepared by flame hydrolysis is very much lower than the number of free hydroxyl groups in silica particles which have not been prepared by flame hydrolysis (in particular prepared by wet chemistry). This difference is based on the fact that in the flame hydrolysis process, which comprises combustion of silicon tetrachloride in an oxygen-hydrogen flame at high temperatures, polysiloxane structures form by direct (thermal) condensation of the silanol groups, as a result of which the number of free hydroxyl groups is reduced.

It is furthermore likewise known that in contrast to silicas produced by wet chemistry, silicas prepared by flame hydrolysis have a virtually pore-free, smooth surface. This feature is also caused by the preparation process.

Silicas prepared by flame hydrolysis, in contrast to silicas prepared by wet chemistry, thus have a lower number of hydroxyl groups per unit area because of the different preparation process, the total surface area of silicas prepared by flame hydrolysis even being still smaller than the total surface area of silicas prepared by wet chemistry. This state of affairs makes it appear plausible that silicas prepared by wet chemistry are functionalized to a far greater degree than silicas of the same particle size prepared by flame hydrolysis. However, a higher surface functionalization of the silica particles which have not been prepared by flame hydrolysis (preferably by wet chemistry) leads to a higher crosslinking density and therefore to a better incorporation of the particles into the matrix of an organic binder system. This better incorporation of the particles appears to be responsible for the better mechanical values determined in our own investigations and the very good abrasion resistance of the dental compositions to be used according to the invention which are based on inorganic filler particles which have not been prepared by flame hydrolysis.

Furthermore, after surface modification of the inorganic filler particles which have not been prepared by flame hydrolysis (preferably prepared by wet chemistry), still free hydroxyl groups normally remain on the surfaces. It seems to be that the quite high number of free hydroxyl groups which remain on filler particles prepared by wet chemistry give the corresponding dental compositions a certain degree of hydrophilicity, which is possibly responsible for such compositions to be used according to the invention flowing on to etched hard tooth structures and penetrating these comparatively well, and thus leading to a firm micromeshing of the plastic on the hard tooth tissue. This effect appears to explain the outstanding experimental adhesion values of compositions to be used according to the invention which are based on inorganic filler particles which have not been prepared by flame hydrolysis.

In our own investigations, it has furthermore been found that it is advantageous for the surface-modified, inorganic filler particles which have not been prepared by flame hydrolysis to be prepared in dispersion and not to dry them before combining with the binder system to be employed. In a different procedure, considerable differences in the physical properties obtained were found in some cases, which is possibly to be attributed to a changed surface structure of the dried particles compared with the non-dried particles.

On the basis of the properties (transmission, flexural strength, abrasion resistance, adhesion to tooth enamel) of the composition to be used according to the invention, in interaction with fluorescence detection methods an outstanding and nevertheless inexpensive prophylaxis of caries can be achieved in particular in the region of dental fissures and pits and in the region of exposed dentine.

Preferably, in a composition according to the invention the organic binder system (b) is configured such that the total amount of the organic binder system (b) comprises (b1) one, two or more monomers chosen from the group consisting of compounds (monomers) of the structure $Q(Y_xZ_e)_b$, wherein:

Q denotes a saturated or olefinically unsaturated polyalicyclic structural element chosen from the group consisting of bicyclic, tricyclic, tetracyclic, pentacyclic and hexacyclic hydrocarbon radicals, wherein optionally one, two or more of the hydrogen atoms of this polyalicyclic structural element Q which are not substituted by substituents $Y_xZ_e$ are substituted by alkyl groups, alkoxy groups, halogen atoms or trifluoromethyl groups, b is a natural number chosen from the group of natural numbers 1, 2, 3 and 4, each Z denotes a structural element which independently of any further structural elements Z is chosen from the group consisting of
—O—(C=O)—CH=CH$_2$, —O—(C=O)—C(CH$_3$)=CH$_2$,
—(C=O)—CH=CH$_2$, —(C=O)—C(CH$_3$)=CH$_2$,
—CH=CH$_2$, —C(CH$_3$)=CH$_2$, and —O—CH=CH$_2$, each index e is a natural number which independently of any further indices e is chosen from the group of natural numbers 1, 2, 3 and 4, each index x denotes independently of any further indices x 0 or 1, each Y denotes in the structure $Q(Y_xZ_e)_b$ where x=1 a structural element which bonds the polyalicyclic structural element Q to e structural elements Z, wherein each Y is chosen independently of any further structural elements Y, and/or (b2) one, two or more polymerizable monomers, wherein the polymerizable monomer or monomers is or are not compounds (monomers) of the structure $Q(Y_xZ_e)_b$ defined above.

Such a compound of the structure $Q(Y_xZ_e)_b$ comprises a polyalicyclic structural element Q which is derived from a corresponding polyalicyclic hydrocarbon. In the context of the present text, this means that b hydrogen atoms of the hydrocarbon are replaced by substituents $Y_xZ_e$ (as described above), and optionally one, two or more of the hydrogen atoms which are not substituted by substituents $Y_xZ_e$ are substituted by alkyl groups, alkoxy groups, halogen atoms or trifluoromethyl groups. The polyalicyclic structural element Q is constituted by carbon ring atoms. Carbon atoms outside the rings are a constituent of substituents.

The "polyalicyclic" structural element Q is a bicyclic, tricyclic, tetracyclic, pentacyclic or hexacyclic hydrocarbon radical, as defined above. The designations "bicyclic", "tricyclic", "tetracyclic", "pentacyclic" and "hexacyclic" in this context correspond to IUPAC nomenclature.

In other words, Q denotes a saturated or olefinically unsaturated polyalicyclic structural element chosen from the group consisting of bicyclic, tricyclic, tetracyclic, pentacyclic and hexacyclic hydrocarbon radicals, wherein none, one, two or more of the hydrogen atoms of this polyalicyclic structural element Q which are not substituted by substituents $Y_xZ_e$ is or are substituted by alkyl groups (in this context preferably C1-C4-alkyl), alkoxy groups (in this context preferably C1-C4-alkoxy), halogen atoms (in this context preferably F) or trifluoromethyl groups.

Preferably, each Y denotes a structural element which in the structure $Q(Y_xZ_e)_b$ where x=1 bonds the polyalicyclic structural element Q to e structural elements Z, wherein each Y is chosen independently of any further structural elements Y.

The sum of the numerical values of the index b and the index e is preferably 3, 4, 5, 6, 7 or 8.

It has been found that the compositions according to the invention are very good dental sealing materials for the purposes mentioned which, compared with a sealing material from the prior art, on dried tooth enamel show very much better flow properties (in particular with respect to the contact angle on the dry tooth enamel), take up very much less water and have good mechanical values (in particular flexural strength).

Preferably, in a composition according to the invention the organic binder system is configured such that the one monomer or one, several or all of the several polymerizable monomers can be polymerized by means of free radicals or without free radicals.

The composite material to be employed or to be used according to the invention is preferably photocurable.

Within a composition according to the invention, the function of the organic binder system (b) is to form a matrix in which the abovementioned filler system is bound.

Component (b1): One, Two or More Monomers of the Structure $Q(Y_xZ_e)_b$ Having at Least One Polyalicyclic Structural Element Components (b1) is formed by one, two or more monomers of the structure $Q(Y_xZ_e)_b$ defined above, wherein Z preferably denotes a structural element which independently of any further structural elements Z is chosen from the group consisting of —O—(C=O)—CH=CH$_2$, —O—(C=O)—C(CH$_3$)=CH$_2$, —(C=O)—CH=CH$_2$ or —(C=O)—C(CH$_3$)=CH$_2$. Compounds of the structure $Q(Y_xZ_e)_b$ are preferred, wherein Z is chosen from the group consisting of —O—(C=O)—CH=CH$_2$, —O—(C=O)—C(CH$_3$)=CH$_2$, i.e. those compounds of the structure $Q(Y_xZ_e)_b$ which contain one, two or more acrylate and/or methacrylate groups, preferably two or more acrylate and/or methacrylate groups.

The polymers and compositions obtainable with the monomers of component (b1) which are preferably to be used according to the invention have a pronounced hydrophobicity, which manifests itself inter alia in a very low water uptake of the polymers and compositions. In addition, the polymers obtainable using the monomers of component (b1) are distinguished by a high mechanical stability, which manifests itself inter alia in a high flexural strength of the polymers. The monomers of component (b1) which are preferably to be used according to the invention, in particular according to the particularly preferred configurations and embodiments, can be processed to polymers which have both a low water uptake and a high flexural strength.

The monomers of component (b1) can be copolymerized with the further monomers of component (b2), the cured polymers or moulding compositions having a low shrinkage, a good adhesion to various substrates, a high resistance to hydrolysis, a low water uptake and a high mechanical strength. The properties mentioned are important in particular in the field of dentistry.

In particular, the preferred and particularly preferred compounds of component (b1) which are to be used render possible a high degree of crosslinking and furthermore can preferably be crosslinked by means of free radicals. Because of their highly functionalized structure, they have a high crosslinking and polymerization probability.

Compounds of component (b1) which are preferably to be employed are those wherein Q denotes a polyalicyclic structural element, preferably a saturated polyalicyclic structural element, which is chosen from the group consisting of bicyclic or tricyclic hydrocarbon radicals, wherein preferably none of the hydrogen atoms of this polyalicyclic structural element Q which are not substituted by substituents $Y_xZ_e$ are substituted.

Monomers $Q(Y_xZ_e)_b$ in which the polyalicyclic structural element Q is derived from one of the following tricyclic hydrocarbons are particularly preferred: tricyclo[5.2.1.0$^{2,6}$] decane (TCD), tricyclo[5.2.1.0$^{2,6}$]dec-3-ene or tricyclo [3.3.1.1$^{3,7}$]decane (adamantane), i.e. compounds which have a TCD framework, a tricyclo[5.2.1.0$^{2,6}$]dec-3-ene framework or an adamantane framework are preferred.

The compounds mentioned which are particularly preferably to be employed, in which the structural element Q denotes a tricyclo[5.2.1.0$^{2,6}$]decane radical, a tricyclo [5.2.1.0$^{2,6}$]dec-3-ene radical, a tricyclo[3.3.1.1$^{3,7}$]decane radical or a bicyclo[2.2.1]heptane radical are preferably those having a tricyclo[5.2.1.0$^{2,6}$]decane framework, a tricyclo [5.2.1.0$^{2,6}$]dec-3-ene framework, a tricyclo[3.3.1.1$^{3,7}$]decane framework or a[2.2.1]heptane framework in which in each case none of the hydrogen atoms of this polyalicyclic structural element Q which are not substituted by substituents $Y_xZ_e$ are substituted.

Compounds $Q(Y_xZ_e)_b$ of component (b1) which are particularly preferably to be employed are those wherein the structural element Q denotes a tricyclo[5.2.1.0$^{2,6}$]decane radical, a tricyclo[5.2.1.0$^{2,6}$]dec-3-ene radical, a tricyclo [3.3.1.1$^{3,7}$]decane radical or a[2.2.1]heptane radical, and the structural element Q very particularly preferably denotes a tricyclo[5.2.1.0$^{2,6}$]decane radical or a tricyclo[5.2.1.0$^{2,6}$]dec-3-ene radical.

Compounds $Q(Y_xZ_e)_b$ of component (b1) which are particularly preferably to be employed are those in which the structural element Q is a tricyclo[5.2.1.0$^{2,6}$]-decane or tricyclo[5.2.1.0$^{2,6}$]-decene structural element and Z is preferably chosen from the group consisting of —O—(C=O)—CH=CH$_2$ and —O—(C=O)—C(CH$_3$)=CH$_2$, wherein in turn the group Z particularly preferably is —O—(C=O)—C(CH$_3$)=CH$_2$.

Particularly preferred compositions comprise as component (b1) one, two or more compounds of the structure $Q(Y_xZ_e)_b$, each of which has a tricyclo[5.2.1.0$^{2,6}$]-decane or tricyclo[5.2.1.0$^{2,6}$]-decene structural element, and Z is preferably chosen from the group consisting of —O—(C=O)—CH=CH$_2$ and —O—(C=O)—C(CH$_3$)=CH$_2$, wherein in turn the group Z particularly preferably is —O—(C=O)—C(CH$_3$)=CH$_2$.

Compounds which are preferably employed are methacrylic acid esters or acrylic acid esters having a tricyclo [5.2.1.0$^{2,6}$]-decane or tricyclo[5.2.1.0$^{2,6}$]-decene structural element chosen from the group consisting of
8,9-bis(acryloxymethyl)tricyclo[5.2.1.0$^{2,6}$]decane
8,9-bis(methacryloyloxymethyl)tricyclo[5.2.1.0$^{2,6}$]decane
8,9-[bis(2-vinyloxyethyl)oxymethyl]tricyclo[5.2.1.0$^{2,6}$]dec-3-ene
8,9-[bis(2-vinyloxyethyl)oxymethyl]tricyclo[5.2.1.0$^{2,6}$]decane
8-hydroxymethyl-9-(2-vinyloxyethyl)oxymethyl]tricyclo [5.2.1.0$^{2,6}$]dec-3-ene
9-hydroxymethyl-8-(2-vinyloxyethyl)oxymethyl]tricyclo [5.2.1.0$^{2,6}$]dec-3-ene
8,9-bis(acryloyloxymethyl)tricyclo[5.2.1.0$^{2,6}$]dec-3-ene
8,9-bis(methacryloyloxymethyl)tricyclo[5.2.1.0$^{2,6}$]dec-3-ene
  diacrylic acid esters or dimethacrylic acid esters of compounds chosen from the group consisting of:
3,8-dihydroxymethyltricyclo[5.2.1.0$^{2,6}$]decane
3,9-dihydroxymethyltricyclo[5.2.1.0$^{2,6}$]decane
4,8-dihydroxymethyltricyclo[5.2.1.0$^{2,6}$]decane
3,8-dihydroxytricyclo[5.2.1.0$^{2,6}$]decane
3,9-dihydroxytricyclo[5.2.1.0$^{2,6}$]decane
4,8-dihydroxytricyclo[5.2.1.0$^{2,6}$]decane
  methacrylic acid esters or acrylic acid esters of compounds from the group consisting of:
poly(hydroxymethyl)tricyclo[5.2.1.0$^{2,6}$]decanyl-siloxanes
oxyalkylated bishydroxymethyltricyclo[5.2.1.0$^{2,6}$]decane
oxyalkylated bishydroxytricyclo[5.2.1.0$^{2,6}$]decane
  methacrylic acid esters or acrylic acid esters, comprising urethane or urea groups, of compounds chosen from the group consisting of:
3,8-dihydroxymethyltricyclo[5.2.1.0$^{2,6}$]decane
4,8-dihydroxymethyltricyclo[5.2.1.0$^{2,6}$]decane
3,9-dihydroxymethyltricyclo[5.2.1.0$^{2,6}$]decane
4,9-dihydroxymethyltricyclo[5.2.1.0$^{2,6}$]decane In the compounds mentioned, hydrogen on the tricyclo [5.2.1.0$^{2,6}$]-decane or tricyclo[5.2.1.0$^{2,6}$]-decene radical can be substituted here by alkyl groups (in this context preferably C1-C4-alkyl), alkoxy groups (in this context preferably C1-C4-alkoxy), halogen atoms (in this context preferably F) or trifluoromethyl groups.

Many of the methacrylic acid esters or acrylic acid esters having a TCD structural element which are listed above and can be polymerized by means of free radicals are known from the prior art.

Y is preferably a structural element which in the structure $Q(Y_xZ_e)_b$ links the polyalicyclic structural element Q with e structural elements Z and comprises a structural element, or consists of this, which is chosen from the group consisting of

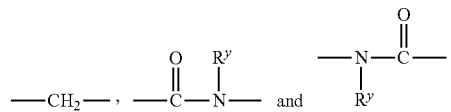

wherein R$^y$ denotes another radical of the compound and
wherein the bond arranged in each case on the left in the formula is closer to the structural element Q and the bond arranged on the right is closer to the structural element Z.

The other radical R$^y$ of a compound of the structure $Q(Y_xZ_e)_b$ preferably to be employed is preferably chosen from the group consisting of hydrogen, linear, branched or ring-comprising structural elements having 1 to 50 C atoms and 0 to 12 hetero atoms, wherein the hetero atoms optionally present are preferably chosen from the group consisting of N and O.

The other radical R$^y$ in this context is preferably chosen from the group consisting of hydrogen, linear, branched or ring-comprising structural elements having 1 to 40 C atoms and 0 to 10 hetero atoms, wherein the hetero atoms optionally present are preferably chosen from the group consisting of N and O.

The other radical R$^y$ in this context is particularly preferably chosen from the group consisting of hydrogen, linear, branched or ring-comprising structural elements having 1 to 35 C atoms and 1 to 10 hetero atoms, wherein the hetero atoms optionally present are preferably chosen from the group consisting of N and O.

Y in this context is preferable a structural element which comprises a structural element, or consists of this, chosen from the group consisting of

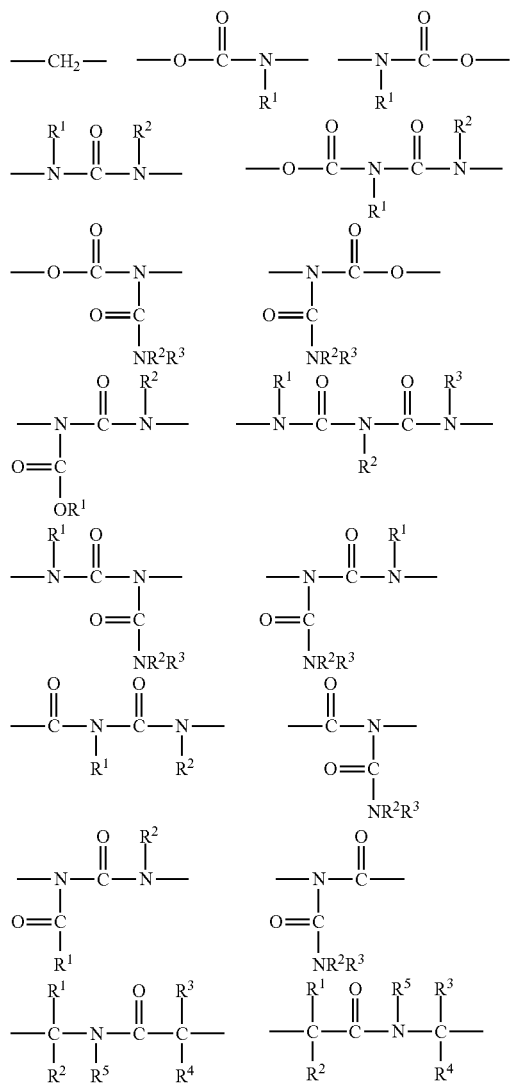

wherein $R^1$, $R^2$, $R^3$, $R^4$ and $R^5$ denote other radicals of the compound, wherein the bond arranged in each case on the left in the formula is closer to the structural element Q and the bond arranged on the right is closer to the structural element Z.

The abovementioned other radicals $R^1$, $R^2$, $R^3$, $R^4$ and $R^5$ of a compound of the structure $Q(Y_xZ_e)_b$ preferably to be employed are, in each case independently of each other, preferably chosen from the group consisting of hydrogen, linear, branched or ring-comprising structural elements having 1 to 30 C atoms and 0 to 10 hetero atoms, wherein the hetero atoms optionally present are preferably chosen from the group consisting of N and O.

The other radicals $R^1$, $R^2$, $R^3$, $R^4$ and $R^5$ in this context are, in each case independently of each other, preferably chosen from the group consisting of hydrogen, linear, branched or ring-comprising structural elements having 1 to 25 C atoms and 0 to 8 hetero atoms, wherein the hetero atoms optionally present are preferably chosen from the group consisting of N and O.

The other radicals $R^1$, $R^2$, $R^3$, $R^4$ and $R^5$ in this context are, in each case independently of each other, particularly preferably chosen from the group consisting of hydrogen, linear, branched or ring-comprising structural elements having 1 to 20 C atoms and 0 to 5 hetero atoms, wherein the hetero atoms optionally present are chosen from the group consisting of N and O.

In compounds of the structure $Q(Y_xZ_e)_b$ which can be synthesized with comparatively little outlay and are preferably to be employed, Y is a structural element which comprises a structural element, or consists of this, which is chosen from the group consisting of

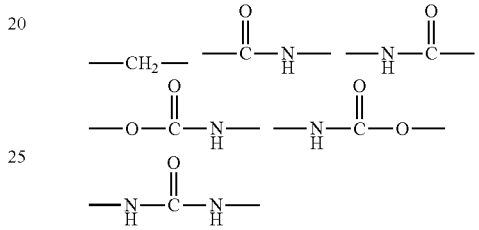

wherein the bond arranged in each case on the left in the formula is closer to the structural element Q and the bond arranged on the right is closer to the structural element Z.

The compound of the structure $Q(Y_xZ_e)_b$ preferably to be employed can be obtained by preparation processes known to the person skilled in the art.

Compounds of the structure $Q(Y_xZ_e)_b$ having an amide structural element which are preferably to be employed can be obtained, for example, by reaction of (i) an educt compound having an isocyanate group and (ii) an educt compound having a carboxylic acid group.

Compounds of the structure $Q(Y_xZ_e)_b$ having a urethane structural element which are preferably to be employed can be obtained, for example, by reaction of (i) an educt compound having an isocyanate group and an educt compound having an alcohol group.

Compounds of the structure $Q(Y_xZ_e)_b$ having a urea structural element which are preferably to be employed can be obtained, for example, by reaction of (i) an educt compound having an isocyanate group and (ii) an educt compound having an amino group.

Compounds of the structure $Q(Y_xZ_e)_b$ having an allophanate structural element which are preferably to be employed can be obtained, for example, by reaction of (i) an educt compound having a urethane group and (ii) an educt compound having an isocyanate group.

Compounds of the structure $Q(Y_xZ_e)_b$ having a biuret structural element which are preferably to be employed can be obtained, for example, by reaction of (i) an educt compound having a urea group and (ii) an educt compound having an isocyanate group.

Compounds of the structure $Q(Y_xZ_e)_b$ having an N-acylurea structural element which are preferably to be employed can be obtained, for example, by reaction of (i) an educt compound having an amide group and (ii) an educt compound having an isocyanate group.

In a particularly preferred embodiment of a composition to be used according to the invention, component (b1) is chosen such that this comprises or consists of bis(methacryloyloxymethyl)tricyclo[5.2.1.0$^{2,6}$]decane and/or bis(acryloyloxymethyl)tricyclo[5.2.1.0$^{2,6}$]decane.

In compositions to be used according to the invention, the methacrylic acid esters are preferred over the corresponding acrylic acid esters because of their higher biological compatibility, i.e. Z in compounds of the structure $Q(Y_xZ_e)_b$ preferably denotes —O—(C=O)—C(CH$_3$)=CH$_2$.

In the context of the present text, (meth)acryl is to be understood as meaning both acryl and methacryl.

Compounds which are particularly suitable for use as monomers in compositions to be used according to the invention are those of the structure $Q(Y_xZ_e)_b$ where x=1 having one, two, three, four or more functional groups, which are chosen from the group consisting of N-acylurea, allophanate and biuret, wherein:

Q denotes a saturated or olefinically unsaturated polyalicyclic structural element chosen from the group consisting of bicyclic, tricyclic, tetracyclic, pentacyclic and hexacyclic hydrocarbon radicals, wherein none, one, two or more of the hydrogen atoms of this polyalicyclic structural element Q which are not substituted by substituents YZ$_e$ is or are substituted by alkyl groups, alkoxy groups, halogen atoms or trifluoromethyl groups;

b is a natural number chosen from the group of natural numbers 2, 3, 4;

each Z denotes a structural element which independently of any further structural elements Z is chosen from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$,

—CH=CH$_2$, —C(CH$_3$)=CH$_2$ and —O—CH=CH$_2$, each index e is a natural number which independently of any further indices e is chosen from the group of natural numbers 1, 2, 3 and 4;

each Y denotes a structural element which in the structure $Q(Y_xZ_e)_b$ where x=1 links the polyalicyclic structural element Q with e structural elements Z and comprises a structural element, or consists of this, chosen from the group consisting of

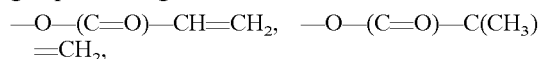

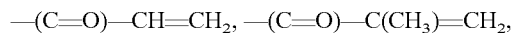

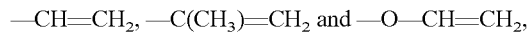

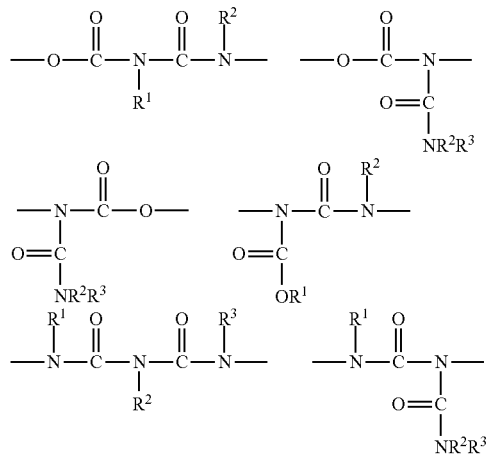

-continued

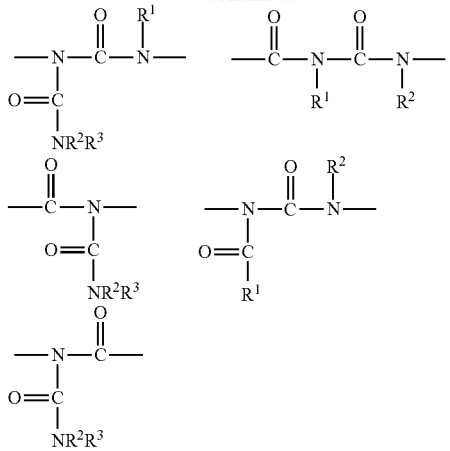

wherein R$^1$, R$^2$ and R$^3$ denote other radicals of the compound, wherein the bond arranged in each case on the left in the formula is closer to the structural element Q and the bond arranged on the right is closer to the structural element Z.

Preferably, such a compound of the structure $Q(Y_xZ_e)_b$ where x=1 comprises two, three, four or more functional groups chosen from the group consisting of N-acylurea, allophanate and biuret.

In a preferred embodiment, each index e denotes a natural number which independently of any further indices e is chosen from the group of natural numbers 2, 3 and 4.

The abovementioned other radicals R$^1$, R$^2$ and R$^3$ of such a compound are, in each case independently of each other, preferably chosen from the group consisting of hydrogen, linear, branched or ring-comprising structural elements having 1 to 30 C atoms and 0 to 10 hetero atoms, wherein the hetero atoms optionally present are preferably chosen from the group consisting of N and O.

The other radicals R$^1$, R$^2$ and R$^3$ of such a compound preferably to be employed are, in each case independently of each other, preferably chosen from the group consisting of hydrogen, linear, branched or ring-comprising structural elements having 1 to 25 C atoms and 0 to 8 hetero atoms, wherein the hetero atoms optionally present are preferably chosen from the group consisting of N and O.

The other radicals R$^1$, R$^2$ and R$^3$ of such a compound preferably to be employed are, in each case independently of each other, preferably chosen from the group consisting of hydrogen, linear, branched or ring-comprising structural elements having 1 to 20 C atoms and 0 to 5 hetero atoms, wherein the hetero atoms optionally present are chosen from the group consisting of N and O.

A compound $Q(Y_xZ_e)_b$ where x=1, preferably a compound $Q(Y_xZ_e)_b$ where x=1 as designated as preferred above or below, to be employed in a composition to be used according to the invention can preferably be prepared by reaction of a first reaction product which is the reaction product from a first reaction of A) a compound of the structure QG$_b$, wherein each G denotes a reactive group which independently of further groups G is chosen from the group consisting of (—CH$_2$)$_n$—NH$_2$, (—CH$_2$)$_n$(OCH$_2$—CHR)$_m$—OH, (—CH$_2$)$_n$—NCO and (—CH$_2$)$_n$—COOH with B) two or more identical or different compounds MZ$_e$, wherein M denotes a structural element which in each case contains one or more grouping(s) which is or are reactive towards the reactive groups G chosen from the group consisting of —NH, —NH$_2$, —OH, —NCO and —COOH, wherein:

R denotes in each case independently of any further R a hydrogen atom or an alkyl radical, m is a natural number chosen from the group of natural numbers of from 0 to 10, each index n is a natural number which independently of any further indices n is chosen from the group consisting of 0 and 1, wherein the compound is a second reaction product from a reaction of the above first reaction product with C) a further compound according to A) or B), wherein each further compound according to A) or B) has the above meaning, independently of the meaning of A) or B) in the first reaction, or the compound is a third reaction product from a reaction of the above second reaction product with D) a further compound according to A) or B), wherein each further compound according to A) or B) has the above meaning, independently of the meaning of A) or B) in the first or second reaction.

A compound preferably to be employed according to a preferred embodiment is a second reaction product from a reaction of the above first reaction product with C) a further compound according to A) or B), wherein each further compound according to A) or B) has the same meaning as in the first reaction, and/or wherein the compound is a third reaction product from a reaction of the above second reaction product with D) a further compound according to A) or B), wherein each further compound according to A) or B) has the same meaning as in the first and/or the second reaction, preferably as in the first and the second reaction.

In a preferred embodiment, m=0.

In compounds preferably to be employed, the linkage between Q and at least one structural element Z is via a bridge which comprises a divalent bridge member, or consists of this, chosen from the group consisting of

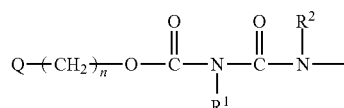
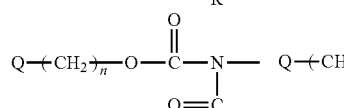
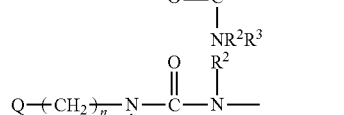
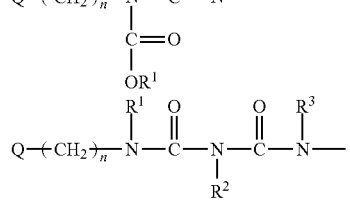

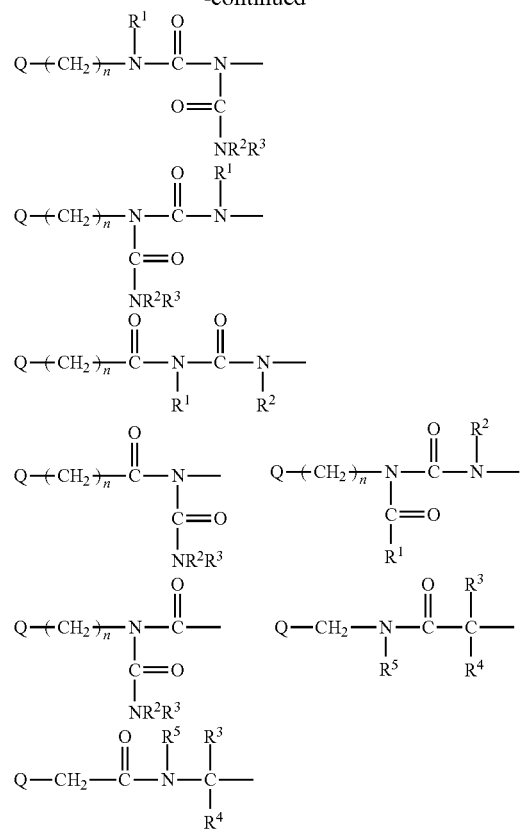

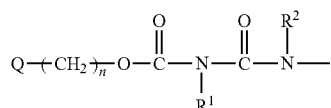
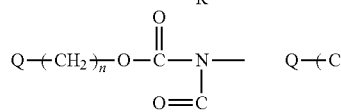
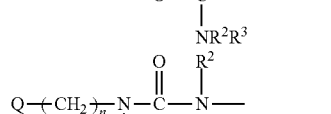
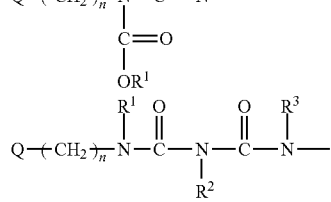

wherein $R^1$, $R^2$, $R^3$, $R^4$, $R^5$ denote other radicals of the compound and Q and the index n have the meaning given above.

The bond arranged in each case on the right in the formula is closer to the structural element Z.

In a preferred embodiment, a compound $Q(Y_xZ_e)_b$ where x=1, preferably a compound $Q(Y_xZ_e)_b$ where x=1 as designated as preferred above or below, preferably to be employed comprises one or more structural elements chosen from the group consisting of

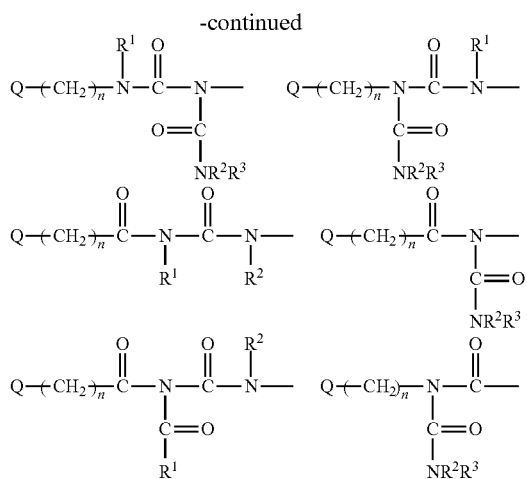

wherein $R^1$, $R^2$ and $R^3$ denote other radicals of the compound (and preferably have the abovementioned preferred meaning) and Q has the abovementioned meaning and the index n is chosen from the group consisting of 0 and 1.

As already mentioned above, compounds which are preferably to be employed are those wherein Q denotes a saturated polyalicyclic structural element which is chosen from the group consisting of bicyclic and tricyclic hydrocarbon radicals, wherein preferably none of the hydrogen atoms of this polyalicyclic structural element Q which are not substituted by substituents $Y_xZ_e$ are substituted.

Compounds which are particularly preferably to be employed are those wherein the structural element Q of the compounds of the structure $Q(Y_xZ_e)_b$ of component (b1) denotes a tricyclo[5.2.1.0$^{2,6}$]decane radical, a tricyclo [5.2.1.0$^{2,6}$]dec-3-ene radical, a tricyclo[3.3.1.1$^{3,7}$]decane radical or a[2.2.1]heptane radical.

Compounds of component (b1) which are preferably to be employed are those wherein Q denotes a tricyclic hydrocarbon radical, wherein preferably none of the hydrogen atoms of this tricyclic hydrocarbon radical which are not substituted by substituents $Y_xZ_e$ (wherein each Y is chosen independently of any further structural elements Y or is omitted) are substituted.

Compounds which are particularly preferably to be employed are those wherein the structural element Q denotes a tricyclo[5.2.1.0$^{2,6}$]decane radical, a tricyclo[5.2.1.0$^{2,6}$]dec-3-ene radical or a tricyclo[3.3.1.1$^{3,7}$]decane radical, further preferably a tricyclo[5.2.1.0$^{2,6}$]decane radical or a tricyclo [3.3.1.1$^{3,7}$]decane radical.

Preferred compounds to be employed according to the invention are those in which
(i) the structural element Z denotes —O—(C=O)—C(CH$_3$)=CH$_2$, wherein the functional groups are allophanate, biuret or acylurea groups, since particularly good results have been achieved with these compounds,
and/or
(ii) the structural element Q denotes a tricyclo[5.2.1.0$^{2,6}$] decane radical.

Compounds which are further preferred are those in which the structural element Z denotes —O—(C=O)—C(CH$_3$)=CH$_2$, wherein the functional groups are allophanate, biuret or acylurea groups and the structural element Q denotes a tricyclo[5.2.1.0$^{2,6}$]decane radical.

Preferred compounds are those in which all the photocurable groups present correspond to the structural element Z.

Preferred compounds are those in which all the terminal polymerizable groups present correspond to the structural element Z. In addition to photocurable groups of the structural element Z, such a compound can also comprise further polymerizable, preferably terminal polymerizable groups which are not photocurable, in particular not under the conventional conditions of photocuring in the dental field. However, this is normally not preferable, since such groups do not contribute towards the desired properties of the product present after the polymerization.

Compounds which are further preferred are those in which at least one structural element $YZ_e$ is chosen independently of the further structural element or elements $YZ_e$, and preferably all the structural elements $YZ_e$ are chosen from the group consisting of

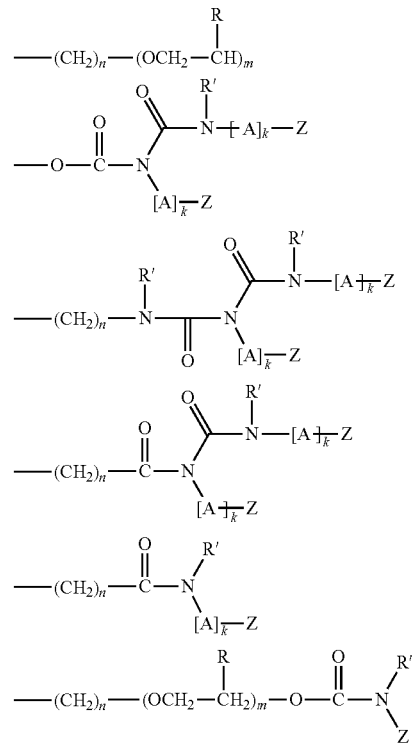

wherein Z, R, m and n have the above meaning, and wherein furthermore:

each A denotes a divalent organic bridge member, each index k is a natural number which independently of any further indices k is chosen from the group consisting of 0 and 1, each R denotes a structural element which independently of any further structural elements R is chosen from the group consisting of H and a structural element (C=O)—NH-(A)$_k$-Z, wherein A, Z and k in turn have the above meanings.

In a preferred embodiment, m=0.

Compounds which are likewise preferred are those in which at least one structural element $YZ_e$ is chosen independently of the further structural element or elements $YZ_e$, and preferably all the structural elements $YZ_e$ are chosen from the group consisting of

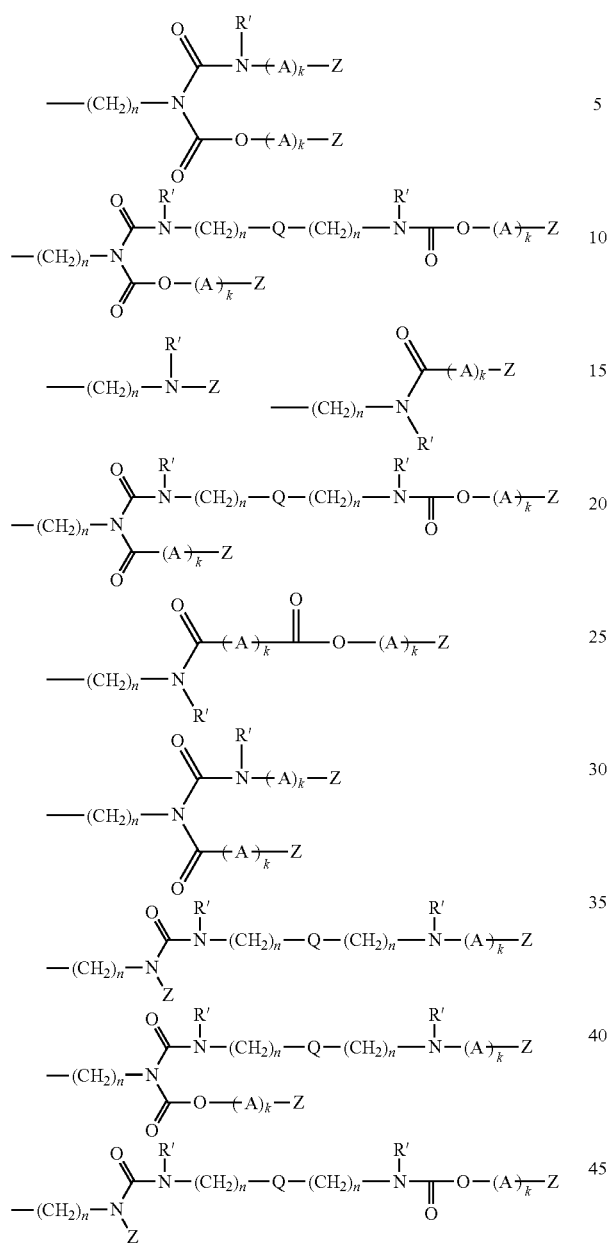

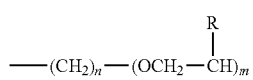

wherein each Q independently of any further structural elements Q has the above meaning and wherein Z, A, k and R' and n have the abovementioned meaning.

A compound $Q(Y_xZ_e)_b$ where x=1, preferably a compound $Q(Y_xZ_e)_b$ where x=1 as designated as preferred above or below, which is particularly suitable for use as a monomer in compositions to be used according to the invention is one wherein at least one structural element $YZ_e$ is chosen independently of the further structural element or elements $YZ_e$, and preferably all the structural elements $YZ_e$ are chosen from the group consisting of

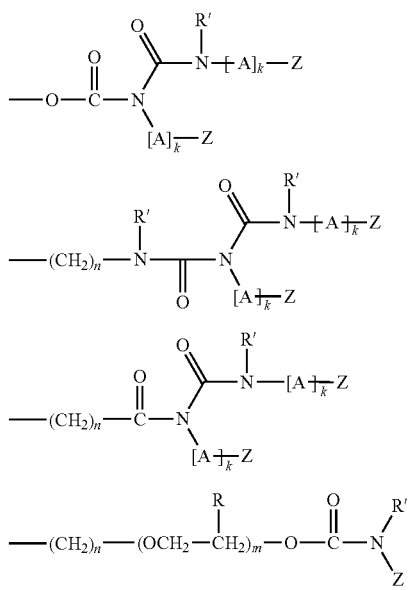

wherein Z, R, m and n have the above meaning, and wherein furthermore:

each A denotes an organic structural element, each index k is a natural number which independently of any further indices k is chosen from the group consisting of 0 and 1, each R' denotes a structural element which independently of any further structural elements R' is chosen from the group consisting of H and a structural element (C=O)—NH-$(A)_k$-Z, wherein A, Z and k in turn have the above meanings.

In a preferred embodiment, a compound $Q(Y_xZ_e)_b$ where x=1, preferably a compound $Q(Y_xZ_e)_b$ where x=1 as designated as preferred above or below, wherein at least one structural element $YZ_e$ is chosen independently of the further structural element or elements $YZ_e$, and preferably all the structural elements $YZ_e$ are chosen from the group consisting of

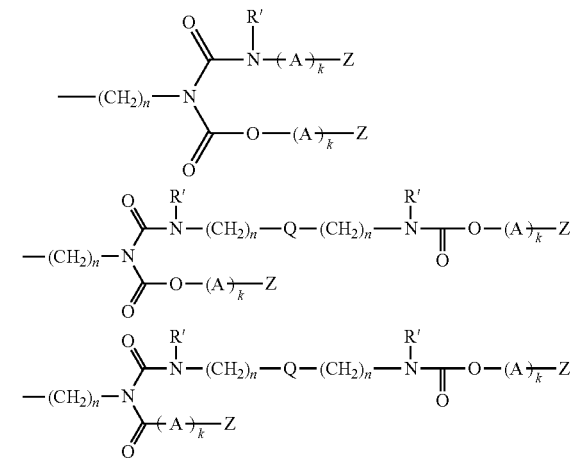

-continued

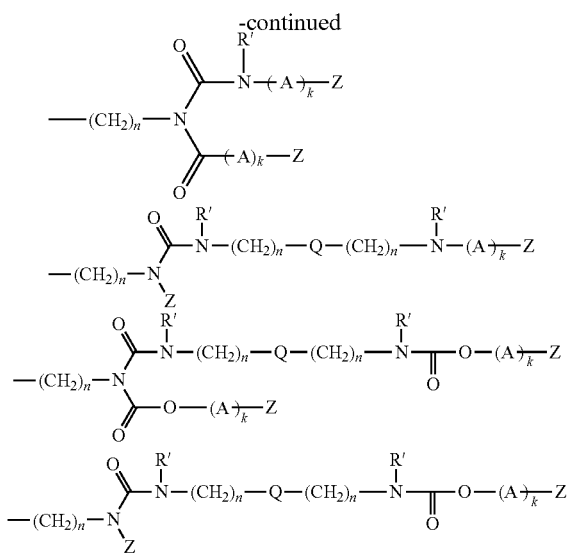

wherein each Q independently of any further structural elements Q has the above meaning, and wherein Z and n have the abovementioned meaning and wherein furthermore:

each A denotes an organic structural element, each index k is a natural number which independently of any further indices k is chosen from the group consisting of 0 and 1, each R' denotes a structural element which independently of any further structural elements R' is chosen from the group consisting of H and a structural element (C=O)—NH-(A)$_k$-Z, wherein A, Z and k in turn have the above meanings.

In this context in turn preferred compounds are those in which each structural element A independently of any further structural elements A is chosen from the group consisting of linear, branched or ring-comprising divalent organic bridge members having 1 to 25 C atoms and optionally 1 to 10 hetero atoms, preferably 1 to 5 hetero atoms, wherein the hetero atoms optionally present are preferably chosen from the group consisting of N and O.

In this context in turn a preferred compound is one in which each structural element A independently of any further structural elements A is chosen from the group consisting of linear, branched or ring-comprising structural elements having 1 to 25 C atoms and 0 to 10 hetero atoms, preferably 1 to 5 hetero atoms, wherein the hetero atoms optionally present are preferably chosen from the group consisting of N and O.

Compounds which are further preferred are those in which each structural element A independently of any further structural elements A is chosen from the group consisting of $C_1$-$C_{20}$-alkylene, $C_1$-$C_{20}$-heteroalkylene, $C_3$-$C_{20}$-cycloalkylene, $C_4$-$C_{20}$-cycloalkylalkylene, $C_2$-$C_{20}$-alkenylene, $C_3$-$C_{20}$-cycloalkenylene, $C_4$-$C_{20}$-cycloalkenylalkylene, $C_4$-$C_{20}$-cycloalkenylenealkylene, $C_3$-$C_{25}$-arylene, $C_2$-$C_{25}$-heteroarylene, $C_4$-$C_{25}$-arylalkylene, $C_4$-$C_{25}$-arylenealkylene, $C_4$-$C_{25}$-arylheteroalkylene, $C_4$-$C_{25}$-aryleneheteroalkylene.

In preferred embodiments, the structural element A comprises one or more of the following atoms or atom groups: —O—, —O—Ar$^1$—CR$^6$R$^7$—Ar$^2$—O—, —NR$^8$—, —N—(C=O)—, —NH—(C=O)—O—, —NH—C(=O)—NH— wherein:

Ar$^1$ and Ar$^2$ denote independently of each other an optionally substituted, in this context preferably mono- or polysubstituted by C1-C4-alkyl radicals, aromatic ring, in this context in turn preferably a phenyl ring, R$^6$, R$^7$ and R$^8$ denote independently of each other hydrogen or a C1-C8 radical, in this context preferably a C1-C4-alkyl radical, in this context in turn preferably methyl or ethyl.

Hydroxy compounds of (meth)acrylates can preferably be employed for the preparation of the said compounds of the structure Q(Y$_x$Z$_e$)$_b$, it also being possible to use mixtures of acrylates and methacrylates. Compounds which are preferably to be employed as reaction partners according to component B), C) or D) are:

alkylene oxide mono(meth)acrylates, such as, for example, ethylene glycol mono(meth)acrylate, diethylene glycol mono(meth)acrylate, triethylene glycol mono(meth)acrylate, tetraethylene glycol mono(meth)acrylate etc., polyalkylene oxide mono(meth)acrylates, such as, for example, polyethylene glycol mono(meth)acrylate, polypropylene glycol mono(meth)acrylate, polybutylene glycol mono(meth)acrylate etc., hydroxyalkyl mono(meth)acrylates, such as, for example, hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate etc., poly(ε-caprolactone)mono(meth)acrylate, poly(γ-caprolactone)mono(meth)acrylate etc., the mono-, di-, tetra-, or penta (meth)acrylates of polyfunctional alcohols, such as glycerol, such as, for example, glycerol di(meth)acrylate (2-hydroxypropyl 1,3-di(meth)acrylate, 3-Hydroxypropyl 1,2-di(meth)acrylate), such as trimethylolpropane, such as, for example, trimethylolpropane di(meth)acrylate, such as pentaerythritol, such as, for example, pentaerythritol tri(meth)acrylate, such as dipentaerythritol, such as, for example, dipentaerythritol penta(meth)acrylate, such as ditrimethylolpropane tri(meth)acrylate, such as neopentyl glycol(meth)acrylate, the (meth)acrylates of alkoxylated or phenoxylated glycerol, in this context preferably the (meth)acrylates of ethoxylated, propoxylated etc. glycerol, trimethylolpropane, pentaerythritol, dipentaerythritol, ditrimethylolpropane etc. and technical grade mixtures thereof, bisphenol A glycidyl(meth)acrylate (Bis-GMA), bisphenol B glycidyl(meth)acrylate, bisphenol C glycidyl(meth)acrylate, bisphenol F glycidyl(meth)acrylate, alkoxylated bisphenol A glycidyl(meth)acrylate (e.g. ethoxylated bisphenol A glycidyl(meth)acrylate) etc.

Isocyanates can also be employed as component B) for the preparation of the compounds. In this context, mono- and diisocyanates are preferred.

Preferred diisocyanates are chosen from the group consisting of cyclohexane-diisocyanate, methylcyclohexane-diisocyanate, ethylcyclohexane-diisocyanate, propylcyclohexane-diisocyanate, methyldiethylcyclohexane-diisocyanate, phenylene-diisocyanate, toluylene-diisocyanate, bis(isocyanatophenyl)methane, propane-diisocyanate, butane-diisocyanate, pentane-diisocyanate, hexane-diisocyanate, such as hexamethylene-diisocyanate or 1,5-diisocyanato-2-methylpentane, heptane-diisocyanate, octane-diisocyanate, nonane-diisocyanate, such as 1,6-diisocyanato-2,4,4-trimethylhexane or 1,6-diisocyanato-2,2,4-trimethylhexane, nonane-triisocyanate, such as 4-isocyanatomethyl-1,8-octane-diisocyanate, decane-di- and -triisocyanate, undecane-di- and -triisocyanate, dodecane-di- and -triisocyanates, Isophorone-diisocyanate, dicyclohexylmethane-4,4'-e-diisocyanate, isocyanatomethylmethylcyclohexyl isocyanate, 1,3-bis(isocyanatomethyl)cyclohexane or 1,4-bis(isocyanatomethyl)cyclohexane.

Preferred monoisocyanates are (meth)acryloyl isocyanate and (meth)acryl-C2-C8-alkyl isocyanates (i.e. (meth)acrylalkyl isocyanates having alkyl spacers which have 2 to 8, particularly preferably 2 to 6 carbon atoms), in this context in turn (meth)acrylethyl isocyanate (2-isocyanatoethyl(meth)acrylate) is preferred.

Monoisocyanates which are reaction products of amino- or hydroxyalkyl(meth)acrylates, the alkyl spacers of which have 1 to 12, preferably 2 to 8, particularly preferably 2 to 6 carbon atoms, and diisocyanates have moreover proved to be advantageous as component B).

For this, an abovementioned diisocyanate is preferably reacted in equimolar amounts with an (characterized above as preferred) amino- or hydroxyalkyl compound of a (meth)acrylate, the hydroxyalkyl compounds in turn preferably being chosen from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Examples which may be mentioned are the reaction products in the molar ratio of 1:1 of hydroxyethyl methacrylate with isophorone-diisocyanate, dicyclohexylmethane-4.4'-diisocyanate or hexamethylene-diisocyanate.

The present invention furthermore relates to the use or employment of an abovementioned compound, preferably in one of the embodiments characterized as preferred or particularly preferred, in a composition according to the invention or to be used according to the invention for the said purposes, preferably in a dental composition.

The present invention also relates to the use of an abovementioned compound of the structure $Q(Y_x Z_e)_b$, preferably in one of the embodiments characterized as preferred or particularly preferred, for the preparation of a composition, preferably a dental composition, in particular a dental sealing material for sealing fissures, for sealing pits and for sealing carious lesions.

Particularly preferred compounds $Q(Y_x Z_e)_b$ where x=1 which can be employed as constituent (b1) of a composition according to the invention can be prepared by the following process. The process comprises the following steps:

In a first reaction, reaction of

A) a compound of the structure $QG_b$, wherein each G denotes a reactive group which independently of further groups G is chosen from the group consisting of $(-CH_2)_n-NH_2$, $(-CH_2)_n-(OCH_2-CHR)_m-OH$, $(-CH_2)_n-NCO$ and $(-CH_2)_n-COOH$, preferably a compound of the structure $QG_b$, wherein each G denotes a reactive group which independently of further groups G is chosen from the group consisting of $-NH_2$, $-CH_2NH_2$, $-OH$, $-CH_2OH$, $-NCO$, $-CH_2NCO$, and $-COOH$, with B) two or more identical or different compounds $MZ_e$, wherein M denotes a structural element which in each case contains one or more grouping(s) which is or are reactive towards the reactive groups G chosen from the group consisting of $-NH$, $-NH_2$, $-OH$, $-NCO$ and $-COOH$ to give a first reaction product,
optionally in a second reaction, reaction of the first reaction product with C) a further compound according to A) or B), wherein each further compound according to A) or B) has the above meaning, independently of the meaning of A) or B) in the first reaction,
to give a second reaction product
and optionally in a third reaction, reaction of the second reaction product with D) a further compound according to A) or B), wherein each further compound according to A) or B) has the above meaning, independently of the meaning of A) or B) in the first or second reaction.

wherein Q, b, Y, Z and e in each case have the abovementioned meaning, and wherein:
R denotes in each case independently of any further R a hydrogen atom or an alkyl radical; preferably, R denotes a hydrogen atom or a linear or branched alkyl radical having 1 to 6 C atoms; further preferably, R denotes a hydrogen atom or a methyl radical,
m is a natural number chosen from the group of natural numbers of from 0 to 10,
each index n is a natural number which independently of any further indices n is chosen from the group consisting of 0 and 1,
wherein the ratio of the total number of NCO groups to the total number of $-NH_2$, $-OH$ and $-COOH$ in the total number of compounds according to A) and B) in the first, optionally second and optionally third reaction is greater than or equal to 1, preferably is in the range of from 1.1:1 to 5:1, further preferably is in the range of from 1.25:1 to 4:1, particularly preferably is in the range of from 1.5:1 to 3:1, and most preferably is in the range of from 2:1 to 2.5:1.

In this context, the ratio of the total number of NCO groups reacted to the total number of $-NH_2$, $-OH$ and $-COOH$ reacted in the total number of compounds according to A) and B) in the first, optionally second and optionally third reaction is preferably in the range of from 1.1:1 to 5:1, further preferably in the range of from 1.25:1 to 4:1, particularly preferably in the range of from 1.5:1 to 3:1, and most preferably in the range of from 2:1 to 2.5:1.

Preferably, the reaction to give the first reaction product, to give the second reaction product and/or to give the third reaction product is carried out in the presence of a catalyst.

Preferred catalysts in this context are tertiary amine or Lewis acids, in this context in turn preferably metal salts of higher fatty acids, in particular dibutyltin dilaurate or tin(II) octoate.

The amount of catalyst in this context is preferably in the range of from 0.01 to 2 wt. %, preferably from 0.08 to 1 wt. %, based on the total amount of the reactants according to A) and B) and optionally C) and optionally D).

The reaction to give the first reaction product, to give the second reaction product and/or to give the third reaction product is preferably carried out in a temperature range of from 0 to 160° C., preferably in the range of from 30 to 140° C. and particularly preferably in the range of from 60 to 120° C. The reaction is preferably carried out under normal pressure (1013 mbar).

A mixture comprising one, two or more different compounds which can be prepared by a process according to the invention is particularly suitable for use as the monomer component in compositions to be used according to the invention.

In the following, the invention is first explained in detail for monomers comprising tricyclic structural elements Q by the example of tricyclo[$5.2.1.0^{2,6}$]decane (TCD) derivatives.

1.) Starting from bis(hydroxymethyl)tricyclo[5.2.1.0$^{2,6}$]decane (TCD-diol)

Bis(hydroxymethyl)tricyclo[5.2.1.0$^{2,6}$]decane is commercially obtainable, for example as a dicidol mixture of the isomeric compounds 3,8-bis(hydroxymethyl)-tricyclo[5.2.1.0$^{2,6}$]decane and 4,8-bis(hydroxymethyl)tricyclo[5.2.1.0$^{2,6}$]decane as well as 3,9-bis(hydroxymethyl)tricyclo[5.2.1.0$^{2,6}$]decane and 4,9-bis(hydroxymethyl)tricyclo[5.2.1.0$^{2,6}$]decane.

Bis(hydroxymethyl)tricyclo[5.2.1.0$^{2,6}$]decanes can be synthesized starting from dicyclopentadiene (tricyclo[5.2.1.0$^{2,6}$]deca-3,8-diene). Dicyclopentadiene is readily accessible preparatively in a Diels-Alder reaction by dimerization of cyclopentadiene. Hydroformylation of dicyclopentadiene then gives bis(hydroxymethyl)-tricyclo[5.2.1.0$^{2,6}$]decane. Depending on the synthesis route, bis(hydroxymethyl)tricyclo[5.2.1.0$^{2,6}$]decanes substituted at different positions can be obtained in a targeted manner. Thus, the publications JP 7-206740, EP 1 112 995 B1 or EP 0 049 631 B1 give instructions as to how, for example, 8,9-bis(hydroxymethyl)tricyclo[5.2.1.0$^{2,6}$]decane can be prepared. DE 103 52 260 B3 on the other hand describes processes for the preparation of 3(4),8(9)-bis(hydroxymethyl)tricyclo[5.2.1.0$^{2,6}$]decane. The notation of the positions of the hydroxymethyl groups 3(4),8(9) denotes 3 or 4, 8 or 9.

The bis(hydroxymethyl)tricyclo[5.2.1.0$^{2,6}$]decane which is commercially obtainable and can be employed as a starting compound for the preparation of monomers thus comprises hydroxymethyl groups both at positions 3 or 4 and in positions 8 or 9. It is now possible to synthesize the corresponding polyether polyols by adding on alkylene oxides, in general in amounts of from 1 to 10 mol, in particular ethylene oxide, propylene oxide, butylene oxide etc., in the presence of basic catalysts by known processes. EP 0 023 686 B1 contains precise preparation instructions for this.

The reaction of 3(4),8(9)-bis(hydroxymethyl)tricyclo[5.2.1.0$^{2,6}$]decanes with isocyanates to give the corresponding urethanes is likewise known. Thus, DE 35 22 006 A1 describes the reaction of 3(4),8(9)-bis(hydroxymethyl)tricyclo[5.2.1.0$^{2,6}$]decane with 2-isocyanatoethyl methacrylate. 2-Isocyanatoethyl methacrylate is commercially obtainable or can be synthesized by phosgenation of dihydro-oxazines in accordance with the preparation instructions from DE 33 38 077 A1.

In a formulation, the reaction product obtained (formula (I)) from 2-isocyanatoethyl methacrylate with 3(4),8(9)-bis(hydroxymethyl)tricyclo[5.2.1.0$^{2,6}$]decane shows a low reaction shrinkage and a high mechanical strength after curing.

Formula (1)

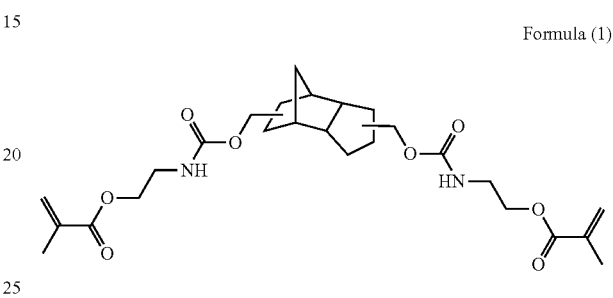

The urethane of the formula (1) still has two reactive hydrogen atoms on nitrogen, which are now reacted further with excess isocyanate in a second reaction stage to form a preferred compound. In this procedure, the allophanate of the formula (2) is first formed as a tetrafunctionalized compound which can be crosslinked by means of free radicals. This monomer in turn also still has hydrogen atoms on nitrogen which are capable of reaction, which on reaction with further isocyanate form the hexafunctionalized allophanate of the formula (3) which can be cured by means of free radicals.

Formula (2)

Formula (3)

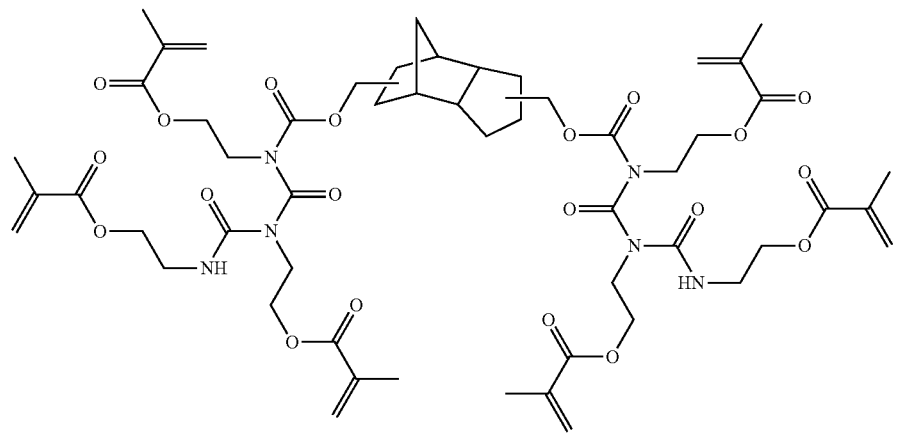

Alternatively, 3(4),8(9)-bis(hydroxymethyl)tricyclo[5.2.1.0$^{2,6}$]decane can also be reacted with methacryloyl isocyanate. Methacryloyl isocyanate is commercially obtainable or obtainable by reaction of methacrylamide with oxalyl chloride, as described in EP 0 143 613 B1. By reaction of 3(4),8(9)-bis(hydroxymethyl)tricyclo[5.2.1.0$^{2,6}$]decane with methacryloyl isocyanate, a compound of the formula (4) is obtained:

Formula (4)

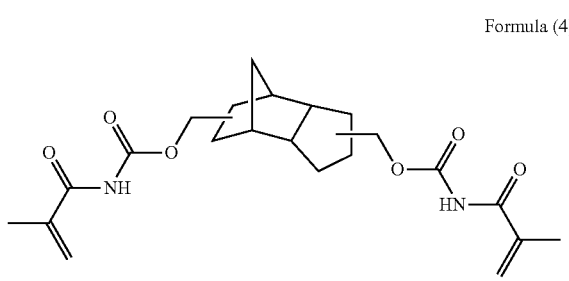

The reactive hydrogen atoms on nitrogen which remain in the compound of the formula (4) can then in turn be reacted in isocyanate reactions to give allophanates. The reaction product with 2-isocyanatoethyl methacrylate (formula (5)) may be shown here by way of example.

Formula (5)

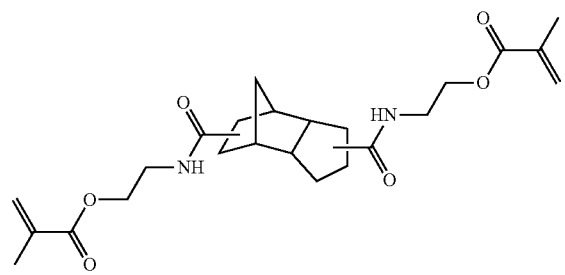

2.) Starting from 3(4),8(9)-bis(carboxylic acid)tricyclo[5.2.1.0$^{2,6}$]decane

3(4),8(9)-Bis(carboxylic acid)tricyclo[5.2.1.0$^{2,6}$]decane can be prepared by simple oxidation of commercially obtainable 3(4),8(9)-bis(formyl)tricyclo[5.2.1.0$^{2,6}$]decane. Reaction of the dicarboxylic acid with 2-isocyanatoethyl methacrylate gives the amide of the formula (8):

Formula (8)

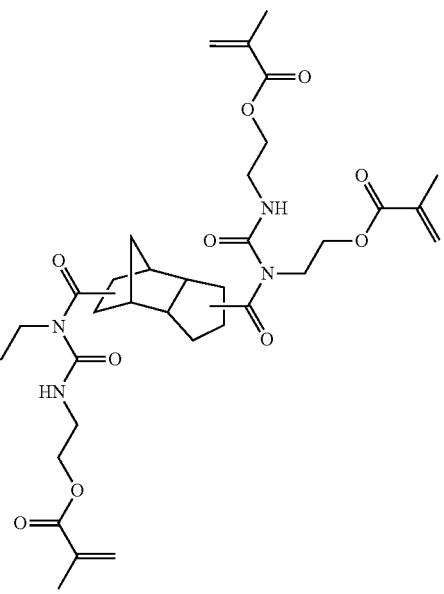

Further reaction of the two reactive amide hydrogen atoms of the amide of the formula (8) with 2-isocyanatoethyl methacrylate gives the acylurea of the formula (9).

Formula (9)

If 3(4),8(9)-bis(carboxylic acid)tricyclo[5.2.1.0$^{2,6}$]decane is reacted with methacryloyl isocyanate, the imide of the formula (10) results. The reactive hydrogen atoms on nitrogen can also be reacted further here in isocyanate reactions.

Formula (10)

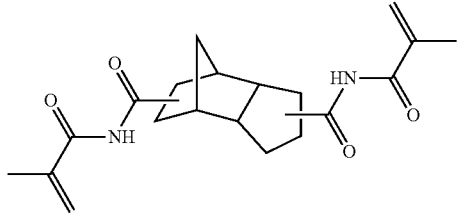

3.) Starting from 3(4),8(9)-bis(isocyanatomethyl)tricyclo[5.2.1.0$^{2,6}$]decane 3(4),8(9)-Bis(isocyanatomethyl)tricyclo[5.2.1.0$^{2,6}$]decane is known per se and is one of the conventional diisocyanate compounds employed in industrial uses (in this context see DE 37 03 120 A1 and WO 2009/065873 A2). The procedure of the second reaction stage of the isocyanate-alcohol reaction can be initiated not only starting from tricyclodecanediol with isocyanatoethyl methacrylate, but also starting from tricyclodecane-diisocyanate and hydroxyethyl methacrylate. By stoichiometric reaction of the two reactants, the urethane of the formula (11) is obtained.

Formula (11)

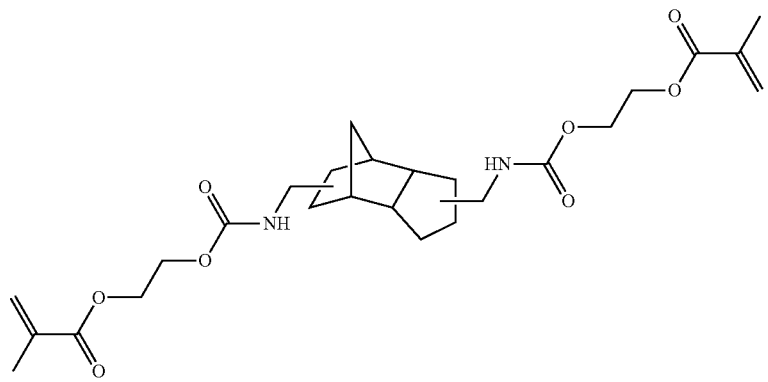

This carbamate (formula (11)) also has two reactive hydrogen atoms on nitrogen, which can be reacted further with an excess of bis(isocyanatomethyl)tricyclo[5.2.1.0$^{2,6}$]decane to give the diisocyanate of the formula (12).

Formula (12)

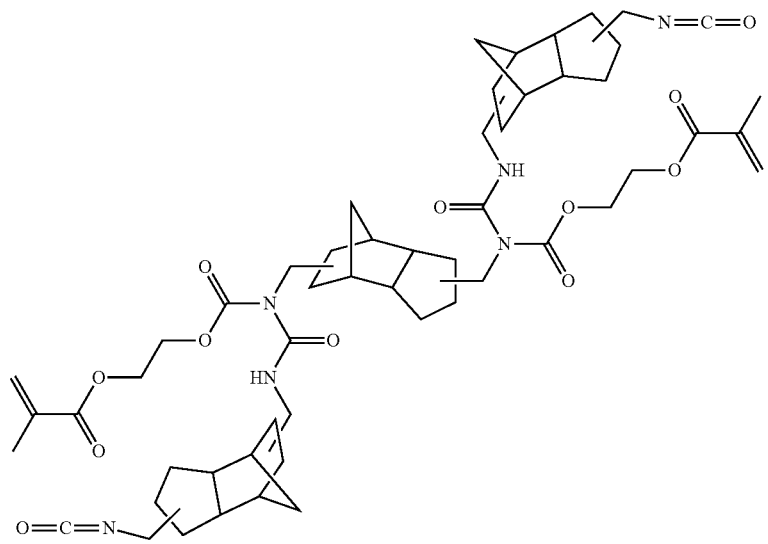

Reaction of the allophanate-diisocyanate (formula (12)) with methacrylic acid gives the compound of the formula (13).

Formula (13)

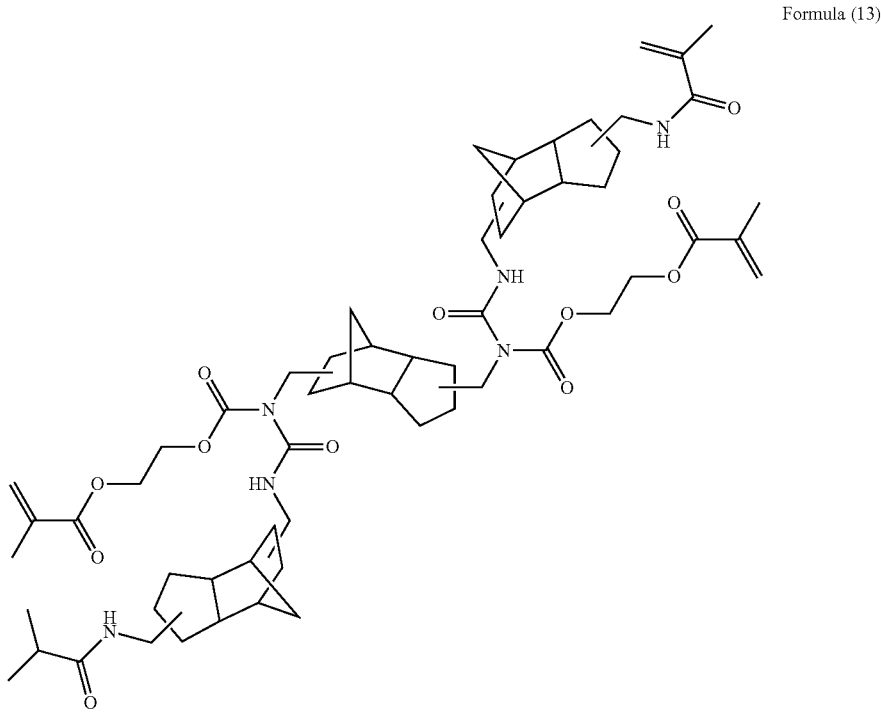

Instead of hydroxyethyl methacrylate, other hydroxy compounds of (meth)acrylates can also be employed in the reactions described by way of example above, it also being possible to use mixtures of acrylates and methacrylates. Thus—analogously to the above example—3(4),8(9)-bis(isocyanatomethyl)tricyclo[5.2.1.0$^{2,6}$]decane can be reacted. Hydroxy compounds of (meth)acrylates which are preferred in this context are alkylene oxide mono(meth)acrylates, such as, for example, ethylene glycol mono(meth)acrylate, diethylene glycol mono (meth)acrylate, triethylene glycol mono(meth)acrylate, tetraethylene glycol mono(meth)acrylate etc., polyalkylene oxide mono(meth)acrylates, such as, for example, polyethylene glycol mono(meth)acrylate, polypropylene glycol mono (meth)acrylate, polybutylene glycol mono(meth)acrylate etc., hydroxyalkyl mono(meth)acrylates, such as, for example, hydroxyethyl(meth)acrylate, hydroxypropyl(meth) acrylate, 2-hydroxypropyl(meth)acrylate, hydroxybutyl (meth)acrylate, 4-hydroxybutyl(meth)acrylate, hydroxypentyl(meth)acrylate, 3-hydroxy-2,2-dimethylpropyl(meth) acrylate, hydroxyhexyl(meth)acrylate, hydroxyheptyl(meth) acrylate, hydroxyoctyl(meth)acrylate, hydroxynonyl(meth) acrylate, hydroxydecyl(meth)acrylate, hydroxyundecyl (meth)acrylate, hydroxydodecyl(meth)acrylate etc., poly(ε-caprolactone)mono(meth)acrylate, poly(γ-caprolactone) mono(meth)acrylate etc., the mono-, di-, tetra-, or penta (meth)acrylates of polyfunctional alcohols, such as glycerol, such as, for example, glycerol di(meth)acrylate (2-hydroxypropyl 1,3-di(meth)acrylate, 3-Hydroxypropyl 1,2-di (meth)acrylate), such as trimethylolpropane, such as, for example, trimethylolpropane di(meth)acrylate, such as pentaerythritol, such as, for example, pentaerythritol tri(meth) acrylate, such as dipentaerythritol, such as, for example, dipentaerythritol penta(meth)acrylate, such as ditrimethylolpropane tri(meth)acrylate, such as neopentyl glycol(meth) acrylate, the (meth)acrylates of alkoxylated or phenoxylated glycerol, in this context preferably the (meth)acrylates of ethoxylated, propoxylated etc. glycerol, trimethylolpropane, pentaerythritol, dipentaerythritol, ditrimethylolpropane etc. and technical grade mixtures thereof, bisphenol A glycidyl (meth)acrylate (Bis-GMA), bisphenol B glycidyl(meth)acrylate, bisphenol C glycidyl(meth)acrylate, bisphenol F glycidyl(meth)acrylate, alkoxylated bisphenol A glycidyl(meth) acrylate (e.g. ethoxylated bisphenol A glycidyl(meth) acrylate) etc.

All of these compounds contain both (meth)acrylate groups and hydroxyl groups. The latter can react with isocyanate groups in the manner described above for the reaction between hydroxyethyl methacrylate and 3(4),8(9)-bis(isocyanatomethyl)-tricyclo[5.2.1.0$^{2,6}$]decane. A high degree of functionalization can thus be achieved in a single reaction step.

3(4),8(9)-Bis(isocyanatomethyl)tricyclo[5.2.1.0$^{2,6}$]decane can be reacted with 2-carboxylic acid-ethyl methacrylate to give the corresponding amide of the formula (16).

Formula (16)

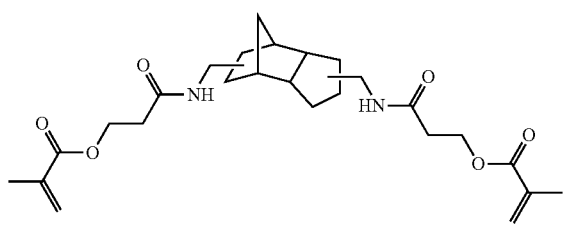

Reaction of the amide of the formula (16) with 2-isocyanatoethyl methacrylate gives the acylurea of the formula (17)

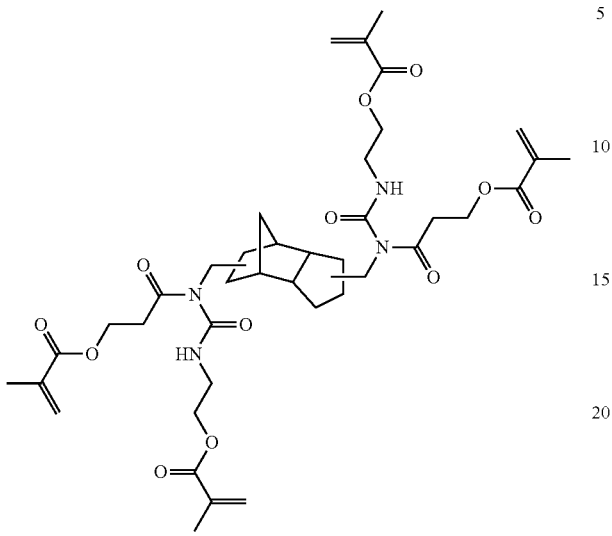

Formula (17)

The amide of the formula (16) can also be reacted with an excess of 3(4),8(9)-bis(isocyanatomethyl)tricyclo[5.2.1.0$^{2,6}$]decane to give the corresponding isocyanate, the isocyanate formed being reacted further with hydroxyethyl methacrylate to give the crosslinkable monomer of the formula (18).

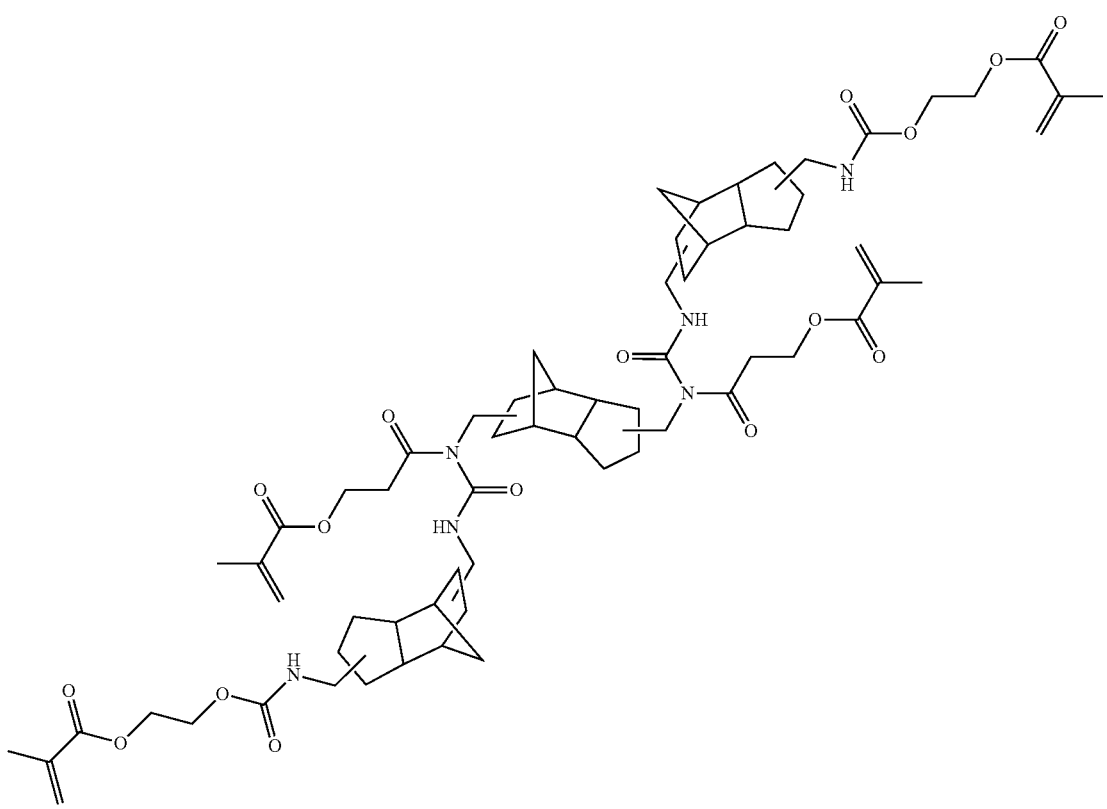

Formula (18)

If 3(4),8(9)-bis(isocyanatomethyl)tricyclo[5.2.1.0$^{2,6}$]decane is reacted with 2-methacryloyloxyethyl hydrogen succinate, the amide of the formula (19) is obtained, which is reacted further with 2-isocyanatoethyl methacrylate to give the acylurea of the formula (20).

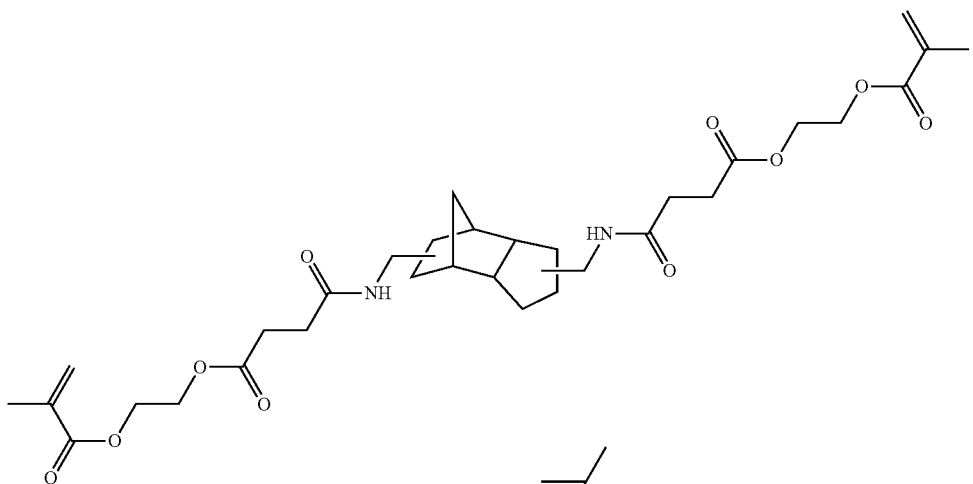

Formula (19)

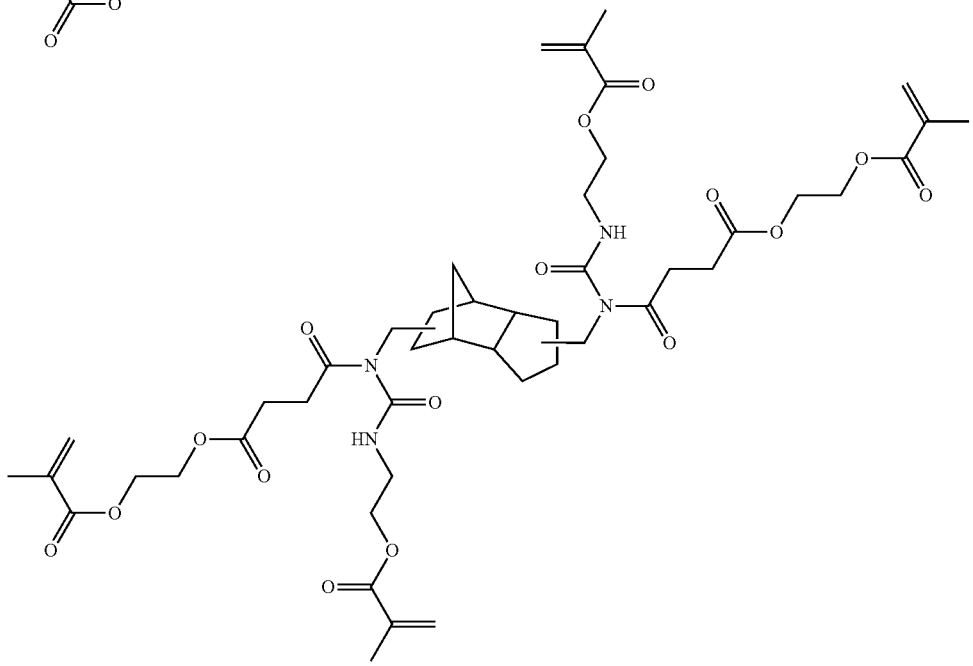

Formula (20)

Further suitable carboxylic acid methacrylates can be obtained by reactions of di- or tetracarboxylic acid mono- or dianhydride with suitable OH-functionalized, curable compounds, such as, for example, 2-hydroxyethyl methacrylate.

4.) Starting from 3(4),8(9)-bis(aminomethyl)tricyclo[5.2.1.0$^{2,6}$]decane

3(4),8(9)-Bis(aminomethyl)tricyclo[5.2.1.0$^{2,6}$]decane is known per se or can be prepared, for example, by reaction of the corresponding tosylates with ammonia. Reaction of 3(4),8(9)-bis(aminomethyl)tricyclo[5.2.1.0$^{2,6}$]decane with 2-isocyanatoethyl methacrylate gives the urea compound of the formula (26) known from EP 0 209 700 A2.

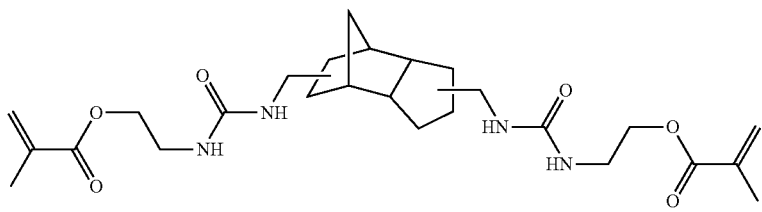

Formula (26)

Here also, there are still active, reactive hydrogen atoms on nitrogen, which react with an excess of isocyanate, for example, to give the biuret of the formula (27).

Formula (27)

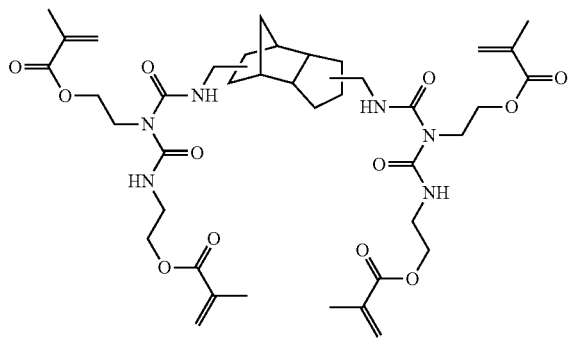

3(4),8(9)-Bis(aminomethyl)tricyclo[5.2.1.0$^{2,6}$]decane can also be reacted with methacryloyl isocyanate to give the corresponding acylurea. Further reaction of the remaining reactive hydrogen atoms on nitrogen with methacryloyl isocyanate gives the biuret of the formula (28).

Formula (28)

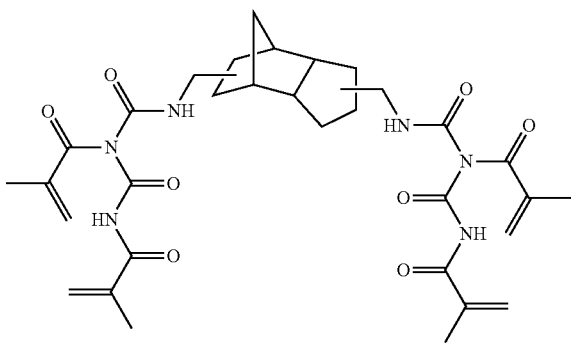

Analogously to the monomers described above, which comprise a polyalicyclic structural element Q derived from tricyclo[5.2.1.0$^{2,6}$]decane, monomers which comprise a polyalicyclic structural element Q derived from tricyclo[3.3.1.1$^{3,7}$]decane (adamantane) can also be prepared. The following reaction products may be shown as examples:

Formula (29)

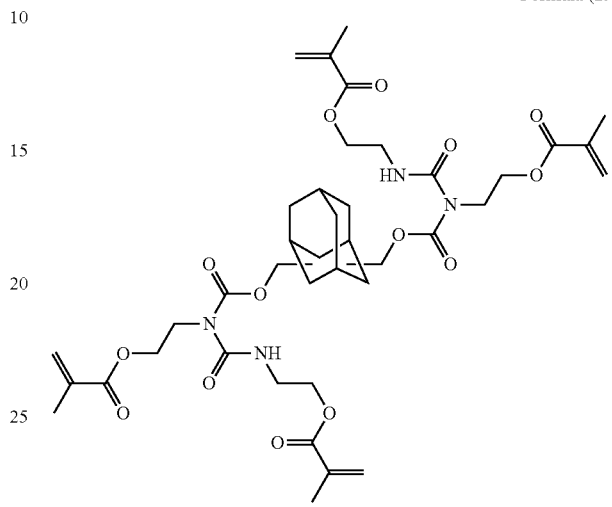

The reaction of the compound of the formula (11) with diisocyanatoadamantane[(bis(isocyanatomethyl)tricyclo[3.3.1.1$^{3,7}$]decane] gives a monomer to be employed, the molecule of which comprises two polyalicyclic structural elements Q which differ from one another, as the following structural formula of the compound of the formula (69) shows.

Formula (69)

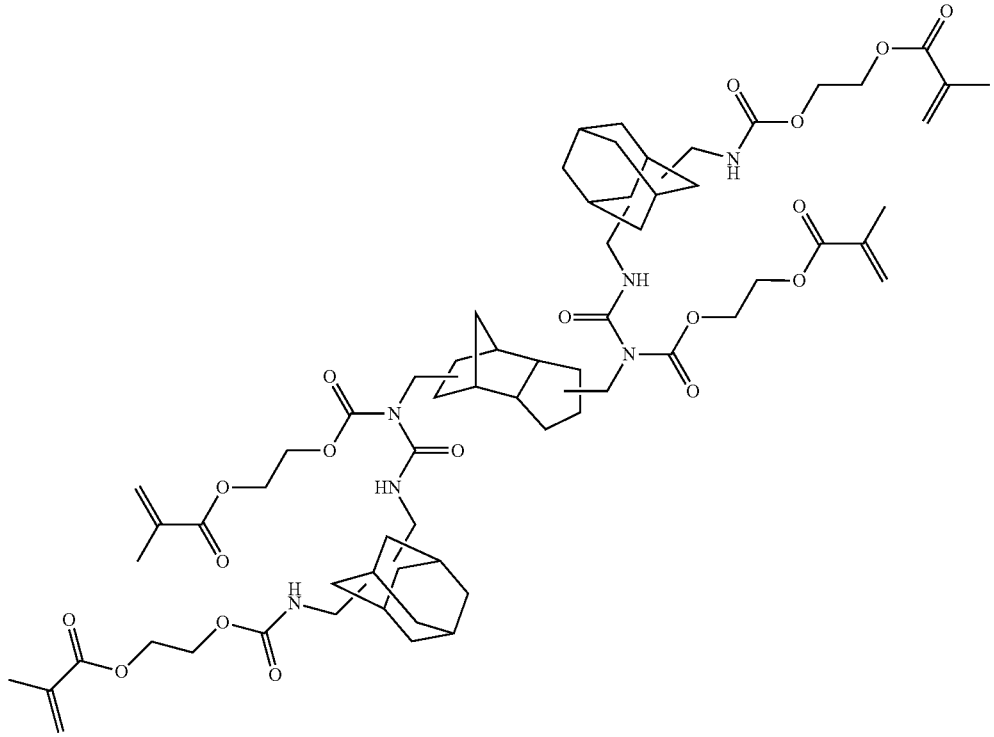

A preferred organic binder system which is to be employed according to the invention comprises as component (b1) one, two or more monomers chosen from the group consisting of compounds (monomers) of the structure $Q(Y_xZ_e)_b$, wherein Q denotes a saturated or olefinically unsaturated polyalicyclic structural element chosen from the group consisting of bicyclic, tricyclic, tetracyclic, pentacyclic and hexacyclic hydrocarbon radicals, wherein none, one, two or more of the hydrogen atoms of this polyalicyclic structural element Q which are not substituted by substituents $YZ_e$ is or are substituted by alkyl groups, alkoxy groups, halogen atoms or trifluoromethyl groups;

b is a natural number chosen from the group of natural numbers 2, 3, 4;

each Z denotes a structural element which independently of any further structural elements Z is chosen from the group consisting of
—O—(C═O)—CH═CH$_2$, —O—(C═O)—C(CH$_3$)═CH$_2$,
—(C═O)—CH═CH$_2$, —(C═O)—C(CH$_3$)═CH$_2$
—CH═CH$_2$, —C(CH$_3$)═CH$_2$ and —O—CH═CH$_2$, each index e is a natural number which independently of any further indices e is chosen from the group of natural numbers 1, 2, 3 and 4, each index x denotes independently of any further indices x 0 or 1, each Y denotes in the structure $Q(Y_xZ_e)_b$ where x=1 a structural element which bonds the polyalicyclic structural element Q to e structural elements Z, wherein each Y is chosen independently of any further structural elements Y, wherein the one, two or more monomers of component (b1) is or are chosen from the group consisting of compounds (monomers) of the structure $Q(Y_xZ_e)_b$ where x=1 having one, two, three, four or more functional groups which are chosen from the group consisting of N-acylurea, allophanate and biuret, wherein:

each Y denotes a structural element which in the structure $Q(Y_xZ_e)_b$ where x=1 links the polyalicyclic structural element Q with e structural elements Z and comprises a structural element, or consists of this, chosen from the group consisting of

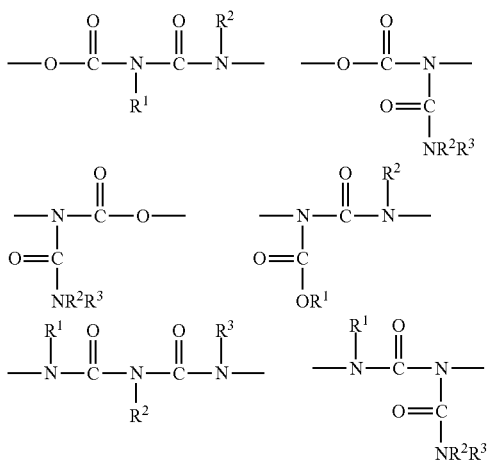

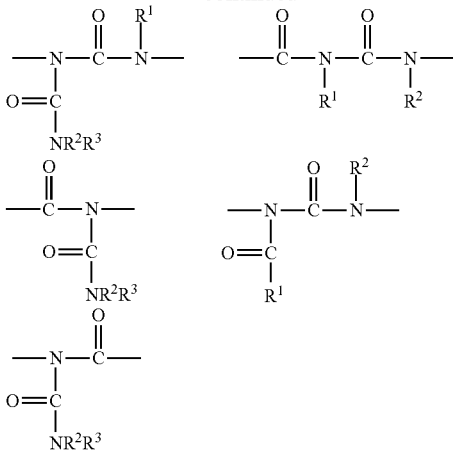

wherein $R^1$, $R^2$ and $R^3$ denote other radicals of the compound, wherein the bond arranged in each case on the left in the formula is closer to the structural element Q and the bond arranged on the right is closer to the structural element Z.

Component (b2): One, Two or More Polymerizable Monomers, wherein the Polymerizable Monomer or Monomers is or are not Compounds (Monomers) of the Structure $Q(Y_xZ_e)_b$ Defined Above The monomers of component (b2) which can be polymerized by means of free radicals are preferably monomers which can be photopolymerized by means of free radicals and preferably have one, two or more ethylenic groups. Preferably, the conventional (meth)acrylate monomers in dental chemistry are employed in a composition according to the invention.

A large number of (meth)acrylate monomers which are suitable for use in a composition according to the invention are mentioned in the patent literature (for example also in DE 39 41 629 A1).

A preferred organic binder system to be employed according to the invention is configured such that the one monomer or one, several or all of the several polymerizable monomers of the monomer component (b2) is or are chosen from the group consisting of acrylates and methacrylates, preferably from the group of methacrylates.

A preferred organic binder system to be employed according to the invention comprises one or more dimethacrylate monomers chosen from the group consisting of ethylene glycol dimethacrylate, 1,6-hexanediol dimethacrylate (HEDMA), triethylene glycol dimethacrylate (TEDMA), 1,12-dodecanediol dimethacrylate, ethoxylated bisphenol A dimethacrylate, polyethylene glycol dimethacrylate, 7,7,9-tri methyl-4,13-dioxo-5,12-diazahexadecane 1,16-dioxydimethacrylate (UDMA), butanediol dimethacrylate, tetraethylene glycol dimethacrylate, neopentyl glycol dimethacrylate, 2-hydroxypropyl 1,3-dimethacrylate, 3-hydroxypropyl 1,2-dimethacrylate, pentaerythritol dimethacrylate, glycerol dimethacrylate (GlyDMA), bisphenol A glycidyl methacrylate (Bis-GMA) and dimethacrylates of dihydroxymethyltricyclo[5.2.1.0$^{2,6}$]decane.

The monomers which are photopolymerizable by means of free radicals can also be hydroxy compounds having at least one ethylenic double bond. In this context, the hydroxy compounds, which are conventionally employed in dental chemistry, of acrylates or methacrylates can preferably be employed. Hydroxy compounds of methacrylates are preferred, and in this context in turn preferably 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane.

Photocurable monomers having ethylenic double bonds based on polysiloxanes, such as are described, for example, in DE 199 03 177 or in DE 44 16 857, can furthermore also be used.

The monomers of component (b2) which can be polymerized by means of free radicals can also be configured as so-called adhesive monomers. 10-(Meth)acryloyloxydecyl dihydrogen phosphate (10-MDP) (EP 0 074 708, EP 1 084 131) has proved to be an adhesion-promoting compound from the group of mono- or diphosphate esters of hydroxyalkyl methacrylates. The phosphoric acid function forms stable, water-insoluble salts with the hydroxyapatite, the calcium being complexed with the aid of the phosphoric acid group. The methylene spacer appears to have a precisely matched length, in order to avoid mutual interference due to steric effects during the bond formation at both ends of the adhesion promoter. This in turn seems to be a prerequisite for being able to wet the substrate surface in an optimum manner and uniformly.

10-MDP can be obtained preparatively by reaction of 10-hydroxydecyl(meth)acrylate with phosphorus oxychloride.

Further compounds of this type are, for example, 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyundecyl dihydrogen phosphate, 20-(meth)acryloyloxyeicosyl dihydrogen phosphate, 1,3-di(meth)acryloyloxypropyl 2-dihydrogen phosphate or 2-(meth)acryloyloxyethylphenyl dihydrogen phosphate.

Instead of a phosphoric acid radical, the polymerizable monomers can also have a diphosphoric acid radical, such as, for example, di(2-(meth)acryloyloxyethyl)pyrophosphate, di(2-(meth)acryloyloxypropyl)pyrophosphate, di(2-(meth)acryloyloxybutyl)pyrophosphate, di(2-(meth)acryloyloxypentyl)pyrophosphate, di(2-(meth)acryloyloxyhexyl)pyrophosphate, di(2-(meth)acryloyloxydecyl)pyrophosphate etc. The corresponding acid halides can also be employed.

In addition to the polymerizable monomers having a phosphoric acid or pyrophosphoric acid radical, corresponding compounds which have a phosphonic acid, a thiophosphoric acid or a sulfonic acid radical can be employed.

Adhesion-promoting monomers can be synthesized analogously, for example from hydroxyalkyl methacrylate or glyceryl dimethacrylate. Mixtures which contain mono-, di- and triesters are thus formed, for example, in the reactions of hydroxyethyl methacrylate with phosphorus oxychloride.

A further type of an adhesive monomer is the phosphoric acid ester of pentaerythritol triacrylate or of dipentaerythritol pentaacrylate (PENTA, U.S. Pat. No. 4,514,342). The ester is prepared from dipentaerythritol monohydroxypentaacrylate and phosphorus oxychloride in the presence of triethylamine.

Other adhesion-promoting compounds (adhesive monomers) which are suitable for use in component (b2) are methacryloyloxyalkyl derivatives of aromatic carboxylic acids. It has been found that in particular trimellitic acid 4-methacryloyloxyethyl ester (4-MET) or trimellitic acid anhydride 4-methacryloyloxyethyl (4-META) can be employed as adhesion-promoting monomers (DE 28 28 381, U.S. Pat. No. 4,148,988, EP 0 684 033, EP 0 684 034). 4-META can be prepared by a dehydrochlorination reaction between hydroxyethyl methacrylate and anhydrous trimellitic acid chloride or by a dehydration reaction between 2-hydroxyethyl methacrylate and trimellitic acid anhydride.

Pyromellitic acid dimethacrylate and pyromellitic acid glycerol dimethacrylate are likewise said to be suitable analogously as an adhesive monomer.

Other methacryloyloxyethyl derivatives of aromatic carboxylic acids which are said to be suitable as adhesive monomers are corresponding compounds of phthalic acid.

Methacryloyloxyethyl derivatives of succinic acid and of maleic acid are furthermore said to be employable as an adhesive monomer.

Further reactive adhesive components which are suitable for use in component (b2) are disclosed in EP 1 148 060, EP 0 909 761 and EP 1 148 071, where polymerizable and hydrolysis-stable acryl-phosphonic acids are described. The involved synthesis route starts with the reaction of formaldehyde and a suitable acrylic acid ester in the presence of a catalyst to form a methylol group in the α-position of the ester and subsequent halogenation of the alcohol with an inorganic acid halide. The α-halomethacrylic acid ester prepared in this way is then reacted with suitable mono- or difunctional phosphonic acid esters which have been protected beforehand. After splitting off the protective group, the polymerizable and hydrolysis-stable acrylphosphonic acid is then obtained, its feature being the terminal oxoethyl acrylate function.

EP 1 346 717 describes tetramethacryloxyethyl pyrophosphate as an adhesion-promoting substance; this compound is also suitable for use in component (b2). The pyrophosphate is said to break up under the aqueous conditions and to hydrolyse to give phosphoric acid esters, which are said to initially ensure a very low pH and are said to help to superficially etch the hydroxyapatite. The phosphoric acid radicals are then said to be neutralized by calcium ions, which are said to migrate out of the dentine, and in this way to form a cement-like adhesive bond to the tooth, while the methacrylate groups can react with the tooth filling material by photopolymerization.

EP 1 721 949 A1 proposes polymerizable derivatives of ethylenediaminetetraacetic acid as adhesion promoters in dental adhesive materials; these are suitable for use in component (b2). The adhesion-promoting effect was demonstrated in EP 1 721 949 A1 by the example of dioxyethoxymethacrylic acid ethylenediaminetetraacetic acid ester.

Preferably, the one monomer or one, several or all of the several polymerizable monomers of component (b2) is or are chosen from the group consisting of acrylates and methacrylates.

Compositions in which the organic binder system is configured such that the one monomer or one, several or all of the several polymerizable monomers is or are chosen from the group consisting of triethylene glycol dimethacrylate (TEDMA), urethane dimethacrylate (7,7,9-trimethyl-4,13-dioxo-3,14-dioxa-5,12-diazahexadecane 1,16-dioxydimethacrylate (UDMA)), glycerol dimethacrylate (GlyDMA) and bisphenol A glycidyl methacrylate (Bis-GMA) have proved to be particularly suitable in our own investigations.

The Organic Binder System (b), Preferably as a Mixture of Components (b1) and (b2):

Preferably, the monomer component (b) is a monomer mixture which comprises both component (b1) and component (b2) or consists of these.

Particularly good results in the context of the present invention are achieved if the weight ratio of the total amount of monomer component (b1) to the total amount of monomer component (b2) is in the range of 4:1 to 1:3, preferably in the range of 3:1 to 1:2, preferably in the range of 2:1 to 2:3, particularly preferably in the range of 3:2 to 2:3 and very particularly preferably in the range of 4:3 to 3:4.

If a composition according to the invention comprises both component (b1) and component (b2), it has proved to be advantageous for bisphenol A glycidyl methacrylate (Bis-GMA) or all compounds having a bisphenol A structural element not to be a constituent of the composition. Bisphenol A glycidyl methacrylate (Bis-GMA) can indeed be employed, but a composition according to the invention preferably does not comprise the compound Bis-GMA. A composition to be employed according to the invention is preferably free from all compounds having a bisphenol A structural element.

A bisphenol A structural element has the following structure:

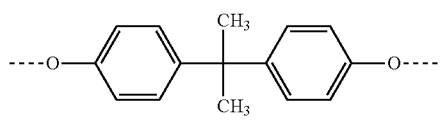

wherein the dashed lines represent covalent bonds to other organic structural elements that are not a part of the Bisphenol A structural element.

If a composition according to the invention comprises both component (b1) and component (b2), very good results are achieved if a mixture of TEDMA and UDMA is employed as monomer component (b2), the weight ratio of TEDMA to UDMA being in the range of 4:1 to 1:4, preferably in the range of 3:1 to 1:3, preferably in the range of 2:1 to 1:2, particularly preferably in the range of 3:2 to 2:3 and very particularly preferably in the range of 4:3 to 3:4.

Particularly good results are achieved if the weight ratio of the total amount of (meth)acrylic acid esters of bis(hydroxymethyl)tricyclo[5.2.1.0$^{2,6}$]decane (monomer component (b1)) to the total amount of the mixture of TEDMA and UDMA (monomer component (b2)) is in the range of 4:1 to 1:3, preferably in the range of 3:1 to 1:2, preferably in the range of 2:1 to 2:3, particularly preferably in the range of 3:2 to 2:3 and very particularly preferably in the range of 4:3 to 3:4, the abovementioned weight ratios of TEDMA to UDMA in turn preferably being established in the monomer component (b2).

The Filler System (a):

In a composition according to the invention, the filler system is configured such that it consists of inorganic filler particles surface-modified by means of organic structural elements or comprises such filler particles, wherein the organic structural elements can be reacted with the monomers to form covalent bonds by means of free radicals or without free radicals, preferably can be reacted with one or more monomers of components (b1) and/or (b2), the filler particles of the filler system having an average particle size in the range between 1 nm and 150 nm. Preferably, the said inorganic filler particles surface-modified by means of organic structural elements are chosen from the group of particles surface-modified by means of organic structural elements and prepared from silicon oxide, zirconium oxide, aluminium oxide and mixed oxides thereof. Particularly preferred particles of the type mentioned are particles prepared (and subsequently surface-modified) by means of wet processes (wet chemistry). The wet processes (wet chemical processes) include in particular sol-gel processes and the process embodiments in which a water-glass is used as the starting substance and is deionized by means of an ion exchanger. In this respect we refer to the statements above.

The said particles of silicon oxide, zirconium oxide, aluminium oxide and mixed oxides thereof which have not been prepared by flame hydrolysis can comprise the conventional impurities. Particularly relevant mixed oxides are the mixed oxides of silicon oxide and zirconium oxide.

Preferably, a composition according to the invention comprises, alongside the preferred inorganic filler particles (as defined above) which have been surface-modified by means of organic structural elements and have not been prepared by flame hydrolysis (preferably prepared by wet chemistry), no further inorganic surface-modified or non-surface-modified filler particles. Preferably, the composition comprises no further filler particles at all.

Compositions according to the invention which comprise more than 40 wt. %, preferably more than 55 wt. %, particularly preferably more than 60 wt. % of filler particles, based on the total weight of the composition, are particularly preferred. In this context, furthermore, the compositions to be used according to the invention preferably comprise inorganic filler particles which have been surface-modified by means of organic structural elements and have not been prepared by flame hydrolysis in a content of from 50 to 100 wt. %, based on the total weight of filler particles employed in the composition according to the invention. Furthermore, for such a composition according to the invention having a content of filler particles in the abovementioned ranges, this can preferably be cured at the same time to give a sealing material which has the transmission designated as preferred above and further preferably also has (i) the flexural strength mentioned and/or (ii) the abrasion mentioned. In this context, in the particularly preferred composition a filler system consisting of or comprising non-aggregated, non-agglomerated filler particles which have been surface-modified by means of organic structural elements and prepared by wet chemistry which are chosen from the group of particles of silicon oxide, zirconium oxide, aluminium oxide and mixed oxides thereof which have been surface-modified by means of organic structural elements and prepared by wet chemistry is dispersed in the organic binder system. The particularly preferred compositions comprises, alongside the said particles, no further filler particles; it preferably comprises more than 40 wt. %, preferably more than 55 wt. %, particularly preferably more than 60 wt. % of the said particles, based on the total weight of the composition. The average particle size of the filler particles of the composition is between 1 nm and 150 nm, preferably between 20 nm and 100 nm, particularly preferably between 30 and 70 nm. The average particle size is determined in this context for the total content of filler particles in the composition. If various types of filler particles are present in the composition, alongside surface-modified, inorganic ones, for example organic or non-surface-modified filler particles, or alongside particles based on silicon oxide also those based on zirconium oxide, all of these filler particles are thus taken into account in the determination of the average particle size. See below for the method for determination of the average particle size.

As already stated above, the particularly preferred composition according to the invention is also transparent to light which is suitable for excitation of a fluorescence both of healthy and of carious hard tooth tissue, and the particularly preferred composition furthermore is transparent to the corresponding fluorescence radiation emitted by the hard tooth tissue.

Additives in the Composition:

A composition according to the invention preferably comprises in the organic binder system one or more additives which render possible or assist in (i) a photocuring and/or (ii) chemical curing of the one or of the several polymerizable monomers.

Examples of additives which render possible or assist in a photocuring of the one or of the several polymerizable monomers are catalysts which have only a photosensitizing action (photosensitizers, photoinitiators) and accelerates (co-initiators), which are preferably employed in combination with photosensitizers.

Examples of suitable photosensitizers are alpha-diketones (e.g. camphorquinone), benzoin alkyl ethers, thioxanthones, benzophenones, acetophenones, ketals, titanocenes, sensitizing dyestuffs etc. The sensitizers can be used by themselves or in combination. Concrete examples of substances of the various classes are to be found, for example, in DE 10 2006 019 092 A1 or in DE 39 41 629 C2.

Examples of suitable accelerators which are employed together with the photosensitizers are tertiary amines (e.g. ethyl p-N,N-dimethylaminobenzoate (DABE), secondary amines, barbituric acids, tin compounds, aldehydes and sulfur compounds. Concrete examples of substances of the various classes are to be found in DE 10 2006 019 092 or in DE 39 41 629 C2.

Further suitable additives (initiators and initiator combinations) are described in DE 601 16 142, which by way of reference are a constituent of the present application.

The photoinitiators which can be used in the context of the present invention are preferably characterized in that they can effect curing of a composition according to the invention by absorption of light in the wavelength range of from 300 nm to 700 nm, preferably from 350 nm to 600 nm and particularly preferably from 380 nm to 500 nm, optionally in combination with one or more co-initiators.

The absorption maximum of camphorquinone (CQ) is approx. 470 nm and thus in the region of blue light. Camphorquinone (CQ) is one of the $PI_2$ initiators and is normally employed together with a co-initiator.

Preferably, a composition according to the invention comprises the combination of an alpha-diketone and an aromatic tertiary amine, and the combination of camphorquinone (CQ) and ethyl p-N,N-dimethylaminobenzoate (DABE) is preferred.

Alternatively, borate salts such as are described, for example, in U.S. Pat. No. 4,772,530, U.S. Pat. No. 4,954,414, U.S. Pat. No. 4,874,450, U.S. Pat. No. 5,055,372 and U.S. Pat. No. 5,057,393, can also be used as photoinitiators.

Further photoinitiators which are suitable in the context of the present invention are described in J.-P. Fouassier, Photoinitiation, Photopolymerization and Photocuring, Hanser Publishers, Munich, Vienna, New York 1995 and in J. F. Rabek (ed.), Radiation Curing in Polymer Science and Technology, vol. II, Elsevier Applied Science, London, New York 1993.

Diverse initiators for a chemical curing, which can also be employed in the context of the present invention, are known to the person skilled in the art. In this respect, reference may be made to EP 1 720 506 by way of example.

Preferred initiators for chemical curing of a composition according to the invention are benzoyl peroxide, lauroyl peroxide and dibenzoyl peroxide. The said chemical initiators, in particular dibenzoyl peroxide, are preferably employed in combination with amines, such as e.g. N,N-dimethyl-p-toluidine, N,N-dihydroxyethyl-p-toluidine and structurally related amines.

The peroxides and the amines in this context are conventionally distributed over two different components of a dental material, the two components and the mixture present after mixing of the components preferably being compositions according to the invention. During mixing of the amine-containing component (so-called base paste) with the peroxide-containing component (so-called initiator or catalyst paste), the free radical reaction is initiated by the reaction of amine and peroxide (redox reaction).

Dual-curing systems are both chemically curable and photocurable systems which conventionally comprise two components, the two components and the mixture present after mixing of the components preferably being compositions according to the invention. Dual-curing systems comprise a combination of photoinitiators and initiators for chemical curing.

For example, the base paste of a dual-curing system can be a composition according to the invention and alongside an amine-containing component additionally comprise a photoinitiator, so that the base paste can be employed either by itself as a photocuring or together with the initiator paste as a photocuring and chemically curing dental material.

Alternatively or in addition to the oxidatively active organic peroxide compounds, in the context of the present invention barbituric acids or barbituric acid derivatives and malonylsulfamides can also be used as redox systems in chemically curing systems.

Of the barbituric acid systems, the so-called "Bredereck's systems" are of great importance. Examples of suitable "Bredereck's systems" and references to the corresponding patent literature are to be found in EP 1 839 640 and in DE 1495520, WO 02/092021 or in WO 02/092023.

Suitable malonylsulfamides are in EP 0 059 451. Preferred compounds in this context are 2,6-dimethyl-4-isobutylmalonylsulfamide, 2,6-diisobutyl-4-propylmalonylsulfamide, 2,6-dibutyl-4-propylmalonylsulfamide, 2,6-dimethyl-4-ethylmalonylsulfamide and 2,6-dioctyl-4-isobutylmalonylsulfamide.

Sulfur compounds in oxidation stage +2 or +4, such as sodium benzenesulfinate or sodium paratoluenesulfinate, can furthermore be employed.

To accelerate the curing, the polymerization can be carried out in the presence of heavy metal compounds, such as Ce, Fe, Cu, Mn, Co, Sn or Zn, copper compounds being particularly preferred. The heavy metal compounds are preferably employed in the form of soluble organic compounds. Preferred copper compounds in this context are copper benzoate, copper acetate, copper ethylhexanoate, copper di(methacrylate), copper acetylacetonate and copper naphthenate.

As a rule, initiators which render possible photocuring and/or chemical curing of the one or of the several polymerizable monomers have no further positive properties after the curing. Rather, there is the possibility that initiators or secondary products thereof which remain after the curing have, after photocuring and/or chemical curing has been concluded, an adverse influence on the mechanical properties of the composition which has cured to give a sealing material. It is therefore advantageous to employ an amount of initiators such that the curing proceeds completely under conditions in practice and at the same time the mechanical properties (e.g. flexural strength and abrasion resistance) are not adversely influenced after the curing.

Compositions according to the invention which comprises in total less than 1.00 wt. %, preferably less than 0.50 wt. %, particularly preferably less than 0.25 wt. %, based on the total weight of the composition, of initiators which (in particular in combination with accelerators) render possible (i) a photocuring and/or (ii) chemical curing of the one or several polymerizable monomers are particularly preferred.

In our own investigations it has been found that initiators which have a phosphine oxide group, such as e.g. phenyl-bis (2,4,6-trimethylbenzoyl)phosphine oxide or 2,4,6-trimethylbenzoyldiphenylphosphine oxide, have a particularly adverse influence on the mechanical properties of the cured composition.

Compositions according to the invention which comprise no initiators or other compounds which have phosphine oxide groups are therefore particularly preferred.

The compositions according to the invention preferably comprise in the organic binder system one or more inhibitors, also called stabilizers. These are added to a curable composition according to the invention in order to avoid a spontaneous polymerization. They react with free radicals which have formed prematurely, which are trapped, and they prevent a premature polymerization and increase the storage stability of the curable, in particular photocurable compositions. The usual inhibitors, which are also preferably employed in compositions according to the invention, are phenol derivatives, such as hydroquinone monomethyl ether (HQME) or 2,6-di-tert-butyl-4-methylphenol (BHT).

Further inhibitors, such as 2,2-diphenyl-1-picrylhydrazyl, galvinoxyl, triphenylmethyl radicals, 2,3,6,6-tetramethylpiperidinyl-1-oxyl radicals (TEMPO) and derivatives of TEMPO or phenothiazine and derivatives of this compound are described in EP 0 783 880 B1. Alternative inhibitors are mentioned in DE 101 19 831 A1 or in EP 1 563 821 A1.

The person skilled in the art is in a position to vary the transmission of a composition according to the invention by adjusting its recipe. Essential recipe parameters here are the weight content of the filler system, the size of the filler particles employed and the presence or absence of additives which colour the composition.

Preparation of compositions according to the invention:

A composition according to the invention comprises a filler system which is dispersed in an organic binder system. Preferably, a composition according to the invention of the above-mentioned type can be prepared by a process having the following steps:

(a) provision or preparation of a colloidal solution (colloidal suspension) of inorganic particles in water,
(b) exchange of the water for an organic solvent which is completely miscible with water (suspending agent),
(c) before or after step (b), modification of the surface of the inorganic particles, so that particles which are surface-modified by means of organic structural elements result, it being possible for the organic structural elements to be reacted with the monomers to form covalent bonds,
(d) partial or complete exchange of the organic solvent which is completely miscible with water for the organic binder system comprising one or more polymerizable monomers, so that the composition to be used according to the invention results.

For preferred processes for the modification of the surface of the inorganic particles, we refer to the statements above.

The present invention also relates to a process for the preparation of a composition to be used according to the invention, having the following steps:

(a) wet chemical preparation of a colloidal solution (colloidal suspension) of inorganic particles by the sol-gel process (see above) or starting from water-glass (see above) in water or another solvent (suspending agent),
(b) conversion of the colloidal solution prepared according to step (a) into a or
provision of the colloidal solution prepared according to step (a) as a
colloidal solution (colloidal suspension) of inorganic particles in an organic solvent which is completely miscible with water (suspending agent),
for example by exchange of the water employed in step (a) for an organic solvent which is completely miscible with water (suspending agent),
(c) before or after step (b), modification of the surface of the inorganic particles, so that particles which are surface-modified by means of organic structural elements result, it being possible for the organic structural elements to be reacted with the monomers to form covalent bonds,
(d) partial or complete exchange of the organic solvent which is completely miscible with water for the organic binder system comprising one or more polymerizable monomers, so that the composition to be used according to the invention results.

The composition according to the invention in use:

Particularly preferably, a composition according to the invention is used in a method for infiltration and/or sealing of hard tooth tissue and for detection of caries in the infiltrated region or under the seal by means of fluorescence and for determination of changes in the state of infiltration or in the seal by means of fluorescence. After the infiltration and/or the sealing of hard tooth tissue (healthy or carious) by means of the composition according to the invention and after the curing of the composition in contact with the hard tooth tissue, the infiltrated region or the seal is subject to the conventional stresses on a tooth surface. Since the composition according to the invention and therefore also the cured seal is based on a plastics matrix, in spite of the high filler content which is preferred according to the invention it is to be expected that, for example, the layer thickness of a seal in a deep fissure decreases in the course of time. The treating dentist can monitor the changes occurring in such a seal (or the corresponding changes in the state of infiltration) in the course of time, in particular the reduction in its thickness, only inadequately even with the aid of the conventional optical aids (in particular a magnifying glass), and is therefore subject to the risk, for example, that he still does not decide on the removal of an almost completely worn seal although this has already become thin and fragile such that it can no longer adequately fulfil its actual purpose, namely of preventing the development of caries. The treating dentist can indeed detect whether caries has already formed under the seal when using the composition according to the invention, but in such a case the removal of the seal no longer follows promptly in the prophylactic sense. It is therefore advantageous to use the composition according to the invention in a combined method which comprises the infiltration and/or sealing of hard tooth tissue and the subsequent detection of caries in the infiltrated region or under the seal by means of fluorescence and the determination of changes in the seal or in the state of infiltration by means of fluorescence. It is surprising knowledge which has been discovered in the context of the present invention that the conventional changes in a seal which has been applied or in an infiltration based on a composition according to the invention can be monitored in an outstanding manner by recording data of a fluorescence measurement on the tooth under investigation. The compositions to be used according to the invention are particularly abrasion-resistant; it is therefore of particular interest to be able to monitor easily and over long periods of time the long-term performance of the seals produced from them or of the regions infiltrated with them.

The present invention accordingly also relates to a method for recording data of a fluorescence measurement on a tooth (in particular the hard tooth tissue of a tooth) having the following steps:

irradiation of an infiltrated and/or sealed tooth surface with excitation radiation which causes the emission of fluorescence radiation, wherein the tooth surface is infiltrated and/or sealed with a composition according to the invention as defined in material terms above, wherein the infiltrant in the infiltrated tooth surface or the seal on the tooth surface is configured such that it is transparent both to the excitation radiation and to the fluorescence radiation emitted, recording of corresponding fluorescence radiation data.

The excitation radiation in this context is preferably radiation with light in the wavelength range of from 600 nm to 670 nm; the fluorescence radiation emitted then advantageously comprises the wavelength already mentioned above of 700 nm, which is typical of carious and healthy hard tooth tissue.

It goes without saying that fluorescence radiation date for those wavelength ranges to which the seal is (adequately) transparent are preferably recorded. For detection of caries in the infiltrated region or under the seal by means of fluorescence, it is thus preferable, for example, to record the fluorescence radiation of a wavelength of 700 nm if an excitation radiation in the wavelength range of from 600 nm to 670 nm is employed. At the same excitation radiation, a wavelength in the range of from 680 nm to 900 nm is preferably recorded for determination of changes in the seal by means of fluorescence.

The comparison of corresponding data which have been recorded at a relatively long interval of time from one another renders possible information on the one hand with respect to the formation of caries in the infiltrated region or under the seal and on the other hand with respect to changes in the seal.

Summarizing, the use of a composition according to the invention in a method for infiltration and/or sealing of hard tooth tissue renders possible on the one hand detection of caries in the infiltrated region or under the seal by means of fluorescence, but on the other hand also routine monitoring of changes in the seal itself. The treating dentist therefore does not rely solely on the conventional optical methods for evaluation of a dental sealing situation, but by using fluorescence techniques can estimate and determine in a very advantageous manner the prompt point in time for replacement of a seal.

In individual cases it has proved appropriate in our own investigations to use compositions according to the invention which additionally comprise a fluorescent dyestuff. However, the additional fluorescent dyestuff should be chosen here such that on excitation by a given excitation radiation it does not completely mask the fluorescence radiation of healthy or carious hard tooth tissue. If a defined fluorescent dyestuff which on excitation by a given excitation radiation emits light of a wavelength which does not overlap to a relevant extent that wavelength which is emitted by carious or healthy hard tooth tissue on excitation with the same excitation radiation is employed, it is possible to observe changes in a seal over a relatively long period of time in a particularly favourable manner. The treating dentist acquires in this manner further information on the dental seal situation, which places him in an even better position to decide whether or not a replacement of a seal which has been applied would be advantageous.

In our own investigations it has been found that compositions according to the invention lead to seals with an outstanding prophylactic and therapeutic action and keep their mechanical properties on the tooth (the hard tooth tissue) for a long time when they are applied in the conventional manner to the tooth, after appropriate pretreatment thereof, and are cured there. Due to the circumstance that a long-term protection is possible with the compositions according to the invention, it seems to be particularly advantageous that methods which render possible a simple monitoring of the seal quality just as much as the required detection of the formation of caries in the infiltrated region or under the seal are now provided by the present invention.

In the method according to the invention, the sealed tooth surface is preferably a tooth surface of a completely sealed tooth or of a tooth sealed in the region of fissures and pits. In particular, the sealed tooth surface is preferably an occlusal, lingual, buccal, distal or mesial tooth surface.

In a particularly preferred method according to the invention, the tooth surface is a tooth surface of a tooth sealed in the region of fissures and pits; in this context the tooth surface is sealed with the (cured) composition such that the sealing material has at least in sections a thickness of 0.5 mm or more, preferably of 1 mm or more. It goes without saying that in this case the composition is preferably configured such that (as stated above for a preferred composition) it can be cured to give a sealing material which, at a layer thickness of 1 mm, has a transmission of 75% or more, preferably of 70% or more, particularly preferably of 80% or more for perpendicularly incident radiation having wavelengths of 655 nm and/or 700 nm, cf. in this context the statements above.

Generally, the compositions according to the invention designated as preferred above are preferably employed in the method according to the invention.

The present invention also relates to a method for treatment of hard tooth tissue, having the following steps:

(A) infiltration and/or sealing of hard tooth tissue with a composition comprising:
   (a) a filler system consisting of or comprising inorganic filler particles surface-modified by means of organic structural elements, wherein the organic structural elements can be reacted with an organic binder system to form covalent bonds,
      wherein the filler particles of the composition have an average particle size in the range between 1 nm and 150 nm,
   (b) an organic binder system comprising one or more polymerizable monomers,
      wherein the filler system is dispersed in the organic binder system (b), and after step (A)

(B) detection of caries in the infiltrated region of the hard tooth tissue or under the seal of the hard tooth tissue by means of fluorescence and/or (C) determination of changes in the seal of the hard tooth tissue by means of fluorescence.

A preferred method according to the invention for treatment of hard tooth tissue is that wherein the (B) detection of caries in the infiltrated region of the hard tooth tissue or under the seal of the hard tooth tissue by means of fluorescence and/or (C) determination of changes in the seal of the hard tooth tissue by means of fluorescence comprises the following steps:

irradiation of the infiltrated or sealed surface of the hard tooth tissue with excitation radiation which causes emission of fluorescence radiation, recording of the corresponding fluorescence radiation data.

A particularly preferred method according to the invention for treatment of hard tooth tissue is that having the following additional step:

comparison of the fluorescence radiation data recorded with standard data.

With respect to the method according to the invention for treatment of hard tooth tissue, the explanations given above and below of the compositions (according to the invention) preferred in the context of the present invention also apply. Preferred embodiments of the method according to the invention for treatment of hard tooth tissue correspond to preferred embodiments of the method according to the invention explained above for recording data of a fluorescence measurement on a tooth; reference is made to the above statements on preferred embodiments of the method.

The present invention also relates to a method for preparation for caries diagnostics and/or for determination of changes in the state of infiltration of a tooth and/or for determination of changes in the seal on a tooth of a patient, having the following steps:

recording of data of a fluorescence measurement according to a corresponding method according to the invention as described above (in particular as designated as particularly preferred above), wherein an infiltrated and/or sealed tooth surface of a patient is irradiated, and comparison of the fluorescence radiation data recorded with standard data, without interaction with the patient.

This of course corresponds to a method according to the invention for recording data of a fluorescence measurement on a tooth having the following additional step for preparation for caries diagnostics and/or for determination of changes in the state of infiltration of a tooth and/or for determination of changes in the seal on a tooth of a patient:

comparison of the fluorescence radiation data recorded with standard data, without interaction with the patient.

In such methods according to the invention for preparation for caries diagnostics, the comparison is preferably automated by means of electronic data processing.

Preferably, the said steps of a method according to the invention for recording data of a fluorescence measurement or for preparation for caries diagnostics and/or for determination of changes in the state of infiltration of a tooth and/or for determination of changes in the seal are repeated with an interval of time of one month or more between the irradiation steps.

The particular results of the comparison of the fluorescence radiation data recorded with the standard data can be passed on or transmitted for the purposes of a subsequent separate diagnosis and/or separate evaluation of the changes found.

A corresponding method of caries diagnostics on a tooth of a patient comprises the following steps:

irradiation of a sealed tooth surface with excitation radiation which causes the emission of fluorescence radiation, wherein the tooth surface is infiltrated and/or sealed with a composition according to the invention as defined in material terms above, wherein the infiltrant in the infiltrated tooth surface or the seal is configured such that it is transparent both to the excitation radiation and to the fluorescence radiation emitted, recording of corresponding fluorescence radiation data, comparison of the fluorescence radiation data recorded with standard data, establishing of significant deviations in the fluorescence radiation data from the standard data, and making a caries diagnosis.

It goes without saying that in this respect the preferred compositions according to the invention are also preferably employed.

The present invention also relates to a kit (a) for infiltration and/or sealing of hard tooth tissue and (b) (i) for detection of caries in the infiltrated region or under the seal by means of fluorescence and/or (ii) for determination of changes in the state of infiltration of a tooth and/or for determination of changes in the seal on a tooth of a patient, comprising:

a composition according to the invention, a device for detection of fluorescence radiation emitted by the hard tooth tissue and/or the seal and/or the infiltrants in the infiltrated region.

With respect to preferred compositions according to the invention, reference may be made to the statements above, which apply here accordingly. Devices for detection of fluorescence radiation from the hard tooth tissue are described above with reference to corresponding publications; such devices are also suitable for detection of fluorescence radiation from the seal or the infiltrants in the infiltrated region, a prerequisite of such a fluorescence radiation of course being the presence of fluorescent substances in the seal or the infiltrants.

The present invention and particularly preferred embodiments are explained in more detail in the following with the aid of determination methods and examples.

EXAMPLES

Method 1

Determination of the Average Particle Size and the Polydispersity of Filler Particles The average (hydrodynamic) particle size of filler particles and their polydispersity is determined for the purposes of the present invention in the conventional manner by means of dynamic light scattering (DLS).

The determination of the average particle size in this context is preferably carried out with the "Partikelsizer ALV-HPPS" apparatus from ALV-Laser Vertriebsgesellschaft mbH, Langen. The measurement is performed with a laser having a wavelength of 632.8 nm. The samples are measured at 25° C. in quartz glass cells with a layer thickness of 10 mm. Isopropanol dried over sodium and freshly distilled is used as the solvent. In this context, the intensity of the scattered light is recorded in relation to the intensity of the primary beam at 13 angles in 10° steps in a range of from 30° to 150°. The software "ALV HPPS 5" is employed for evaluation of the dynamic light scattering. The evaluation of the correlation function is made by means of the evaluation methods of simple fit (for monodisperse samples (polydispersity<0.1)) and regularized fit (for polydisperse distributions (polydispersity>0.1)).

Method 2

Determination of the Adhesion of the Cured Composition According to the Invention to Tooth Enamel The determination of the adhesion (see Example 17 and the associated table) is carried out analogously to ISO TS 11405: 2003 E. For this, tooth enamel from cattle teeth is abraded with abrasive paper (6000 grain size). The abraded tooth enamel is then treated with a phosphoric acid etching gel (35% strength) for 30 seconds, rinsed with a water spray for 20 seconds and blown dry with compressed air for a further 10 seconds. A silicone ring having an internal diameter of 5 mm is then placed on the dry, superficially etched tooth enamel surface. The silicone ring is filled with the composition of which the adhesion to tooth enamel is to be tested. In the case of photocuring compositions, the material is allowed to act for 10 seconds. The material is then cured at a suitable wavelength for 20 seconds. After curing of the composition, the silicone ring is removed. The test specimen produced in this way is stored in a steam bath at 37° C. for 24 hours, before it is measured with a Reinhardt shear bond apparatus (Reinhardt K J, Phillip Journal, 3-4, 1997, 101-104) with an advance speed of 1 mm/s. The adhesion is stated in MPa.

For determination of the adhesion after temperature cycles ("adhesion TC"), the test specimen is exposed to 3,000 temperature cycles between 5 and 55° C. (for this it is placed alternately in each case for 1 minute in a bath of temperature 55° C. and then for 1 minute in a bath of temperature 5° C.) and is then measured.

Method 3

Determination of the Flexural Strength of the Cured Composition According to the Invention The determination of the flexural strength (see Example 17 and the associated table) is carried out analogously to ISO 4049. For this, a test specimen having dimensions of 2×2 mm is measured. In the case of photocuring compositions, curing is carried out at a suitable wavelength for 20 seconds.

For determination of the flexural strength after temperature cycles ("flexural strength TC"), the test specimen is exposed to 3,000 temperature cycles between 5 and 55° C. (for this it is placed alternately in each case for 1 minute in a bath of temperature 55° C. and then for 1 minute in a bath of temperature 5° C.) and is then measured.

Method 4

Determination of the Abrasion

For determination of the abrasion (see Example 17 and the associated table) the ACTA (Academic Center of Dentistry Amsterdam) 3 media abrasion method is carried out in accordance with J. Dent. Suppl. 1, 1994, 22, 21-27 (200,000 cycles).

Method 5

Determination of the Specific Surface Area by the BET Method

The determination of the specific surface area is carried out by gas adsorption by the BET method in accordance with DIN ISO 9277. The volumetric method (point 6.3.1 of DIN ISO 9277) is used. Helium with a purity of >99.99% is used as the measuring gas.

Method 6

Determination of the Transmission at Certain Wavelengths

The determination of the transmission is carried out on a Lambda 650 UV-Vis spectrometer from PerkinElmer (Rodgau). For this, a test specimen having dimensions of 10×10×1 mm is produced and is clamped in a transmission holder such that the incident radiation impinges perpendicularly on the 10×10 mm surface of the test specimen and radiates through the test specimen (sample thickness 1 mm). The measurement is performed once without the test specimen and once with the test specimen. The transmission corresponds to the quotient between the wavelength intensity $I_0$ without the test specimen and the wavelength intensity/with the test specimen at the corresponding wavelength. The transmission is preferably stated in per cent [%].

Method 7

Determination of the Transmission in the Visual Region

The determination of the transmission in the visual region is carried out on a Color Flex d/8° colorimeter from HunterLab. For this, a test specimen having a thickness of 1 mm and a diameter of 20 mm is produced in a Teflon mould. For curing, the composition is irradiated with blue light for 30 minutes. The measurement is performed at room temperature; the relative atmospheric humidity admissible for the measurement is between 5 and 85%. The measurement results are evaluated with the software "Easymatch QC" (version 4.3) from HunterLab. Before measurement of the sample, the apparatus is calibrated in accordance with the instructions for use. The sample is then measured four times against a white background and four times against a black background. The transmission is calculated according to the formula [Transmission=100−opacity]. The transmissions measured are called "transmission [%] (Vis)" in the following and are stated without a defined wavelength.

Method 8

Determination of the Flow Properties: Contact Angle on Dry Tooth Enamel

The flow properties were determined by measurement of the contact angle on dry tooth enamel.

An extracted human molar was used for the contact angle measurements (CA, in degrees [°]) on dry tooth enamel. Before the measurement, this was dried by wiping with a cellulose cloth. A drop of the material to be investigated was then applied to the enamel region of the tooth. The contact angle was then determined over a period of time of 30 seconds using a contact angle meter (DSA 100, Krüss).

Method 9

Determination of the Water Uptake

The water uptake was determined analogously to ISO 4049. For this the compositions were introduced without air bubbles into corresponding Teflon moulds, covered with films and glass plates, and the excesses were pressed out with a thumbscrew. The test specimens having a diameter of 15.0±0.1 mm and a height of 1.0±0.1 mm were photocured in segments. The test specimens were then stored in a desiccator at 37° C. After 22 hours the test specimens were removed, brought to 23° C. in a second desiccator for 2 hours and then weighed to 0.1 mg. This cycle was repeated until a constant weight, m, was reached.

After complete drying, the diameter was measured twice at right angles to one another with a measurement accuracy of 0.01 mm and the average diameter was calculated therefrom. The thickness of the test specimen was measured to 0.01 mm in the middle and at four places on the edge lying at the same distance. The volume, V, was calculated from the average diameter and the average thickness.

The test specimens were then stored in water at 37° C. for 7 days. Thereafter, the test specimens were removed, rinsed with water and dabbed until moisture was no longer visible on the surface. The test specimens were waved backwards and forwards in air for 15 s and weighed 1 min after being removed from the water. This weight is stated as $m_2$.

The test specimens were then stored again in a desiccator at 37° C. After 22 hours the test specimens were removed, brought to 23° C. in a second desiccator for 2 hours and then weighed to 0.1 mg. This cycle was repeated until a constant weight, $m_3$, was reached.

The water uptake, $W_{sp}$, was calculated according to the following equation:

$$W_{sp} = \frac{m_2 - m_3}{V}$$

In this equation
$m_2$ is the weight of the test specimen after storage in water for 7 days in µg;
$m_3$ is the weight of the redried test specimen in µg;
V is the volume of the test specimen in mm³

Synthesis Example

Synthesis of bis(methacryloyloxymethyl)tricyclo [5.2.1.0$^{2,6}$]decane (Monomer According to Component (b1))

0.95 g (4.84 mmol) of 3(4),8(9)-bis(hydroxymethyl)tricyclo[5.2.1.0$^{2,6}$]decane were dissolved in 10 ml of toluene, and 0.04 g of BHT and 0.103 g of the catalyst solution were added. 3.00 g (19.34 mmol, 4 equivalents) of isocyanatoethyl methacrylate, dissolved in 10 ml of toluene, were added dropwise, while stirring. When the addition had ended, the dropping funnel was exchanged for a reflux condenser and the reaction mixture was heated to 120° C. and the progress of the reaction was monitored by means of IR spectroscopy. After 72 hours, a further 0.102 g of catalyst solution was added and the mixture was heated further until the isocyanate band was no longer detected. The solvent was removed on a rotary evaporator. The allophanate of the formula (2) was obtained in a yield of 3.83 g (4.69 mmol, 97%) as a slightly yellowish oil.

Example 1

General Instructions for the Preparation of a Composition According to the Invention which can be Polymerized by Means of Free Radicals 1.1 Preparation of Silica Particles Surface-Modified by Means of Organic Structural Elements:

A colloidal dispersion of inorganic filler particles of suitable average particle size prepared by wet chemistry is provided, an organic, water-soluble matrix, for example isopropanol, being employed as the dispersing agent.

The dispersion is mixed with
(a) a sufficient amount of a surface-modifying agent which has on the one hand alkoxysilane groups and on the other hand organic group which can be reacted, to form covalent bonds, with monomers which can be polymerized by means of free radicals (such a surface-modifying agent is e.g. 3-methacryloyloxypropyl-trialkoxysilane),
(b) two to ten times the molar amount of water, based on the surface-modifying agent, and
(c) approx. 1 wt. %, based on the surface-modifying agent, of methacrylic acid.

The resulting mixture is stirred at 50-80° C. for at least 8 h, so that the surface modification of the inorganic filler particles employed can proceed to completion.

1.2 Preparation of the Composition:

An organic binder system which comprises one or more monomers which can be polymerized by means of free radicals is then added to the intermediate product mixture obtained according to Example 1.1, which comprises surface-modified inorganic filler particles, prepared by wet chemistry, in a dispersing agent. Volatile constituents of the resulting mixture (in particular water, the dispersing agent of the inorganic filler particles initially employed and the alcohol formed by reaction of the alkoxysilane with water) are separated off in vacuo.

Example 2

Instructions for the Preparation of a Composition According to the Invention

For the preparation of a preferred composition according to the invention, the following are employed:
2.1 Constituents of the organic binder system (monomer according to component (b2)):
  60 g of glycerol dimethacrylate (GlyDMA),
  50 g of triethylene glycol dimethacrylate (TEDMA),
  60 g of bisphenol A glycidyl methacrylate (Bis-GMA)
2.2 Materials for the preparation of silica particles which have been surface-modified by means of organic structural elements and have not been prepared by flame hydrolysis:
  864 g of an ethanolic, 20% strength suspension of silica particles which have not been prepared by flame hydrolysis (having an average particle size of 40 nm),
  40 g of gamma-methacryloyloxypropylsilane (23%, based on the solids content, for surface modification),
  0.4 g of methacrylic acid and
  18 g of water.
2.3 Additives:
  0.25 g of 2,6-di-tert-butyl-4-methylphenol (BHT),
  2.5 g of 2-(2H-benzotriazol-2-yl)-p-cresol (Tinuvin P),
  0.5 g of camphorquinone (CQ) and
  2.4 g of ethyl p-N,N-dimethylaminobenzoate (DABE).

Silica particles which have been surface-modified by means of organic structural elements and have not been prepared by flame hydrolysis are prepared from the materials mentioned under 2.2 in accordance with Example 1 (general instructions), point 1.1.

These silica particles (in the form of the intermediate product mixture, i.e. in the dispersing agent), the constituents according to 2.1 and the additives according to 2.3 are mixed thoroughly with one another. Volatile constituents of the resulting mixture (in particular water, the dispersing agent of the inorganic filler particles initially employed and the alcohol formed by reaction of the alkoxysilane with water) are separated off in vacuo.

A composition according to the invention in paste form results, which is photocurable by irradiation with light having a wavelength of 470 nm.

Examples 3 to 9

Instructions for the Preparation of Compositions to be Used According to the Invention Having Different Filler Contents The preparation is carried out analogously to Example 2, but various amounts of the surface-modified silica particles (having a particle size of 40 nm) which have been surface-functionalized according to Example 1 are used.

| | |
|---|---|
| Example 3 | 19.5 g of silica particles (corresponds to 10 wt. %) |
| Example 4 | 43.9 g of silica particles (corresponds to 20 wt. %) |
| Example 5 | 75.3 g of silica particles (corresponds to 30 wt. %) |
| Example 6 | 117.1 g of silica particles (corresponds to 40 wt. %) |
| Example 7 (corresponds to Example 2) | 175.7 g of silica particles (corresponds to 50 wt. %) |
| Example 8 | 263.5 g of silica particles (corresponds to 60 wt. %) |
| Example 9 (comparison) | 0 g of silica particles (corresponds to 0 wt. %); composition without a filler content |

Examples 10 to 16

Instructions for the Preparation of Compositions to be Used According to the Invention Having Different Filler Contents The preparation of the compositions to be used according to the invention was carried out analogously to Example 2, but in all the Examples 10 to 15 the constituents of the organic binder system were replaced by the following constituents:

Constituents of the organic binder system (instead of the constituents according to 2.1; combination of monomers according to components (b1) and (b2)):
60 g of glycerol dimethacrylate (GlyDMA),
50 g of triethylene glycol dimethacrylate (TEDMA),
60 g of bis(methacrylolyoxymethyl)tricyclo[$5.2.1.0^{2,6}$]decane.

The amounts of the surface-modified silica particles (having a particle size of 40 nm) which had been surface-functionalized according to Example 1 were likewise varied according to the following table.

| | |
|---|---|
| Example 10 | 19.5 g of silica particles (corresponds to 10 wt. %) |
| Example 11 | 43.9 g of silica particles (corresponds to 20 wt. %) |
| Example 12 | 75.3 g of silica particles (corresponds to 30 wt. %) |
| Example 13 | 117.1 g of silica particles (corresponds to 40 wt. %) |
| Example 14 | 175.7 g of silica particles (corresponds to 50 wt. %) |
| Example 15 | 263.5 g of silica particles (corresponds to 60 wt. %) |
| Example 16 (comparison) | 0 g of silica particles (corresponds to 0 wt. %); composition without a filler content |

Comparative Example 1 cf. WO 2007/028159 A2, Example 1

9.5 g of Nanocryl D120 (50 wt. % of $SiO_2$, 20 nm particles, dispersed in alkoxylated pentaerythritol tetramethacrylate; Hanse Chemie) and 0.5 g of Lucirin TPO (2,4,6-trimethylbenzoyldiphenylphosphine oxide; Aldrich) were blended at 50° C. A transparent composition which is photocurable by irradiation with light having a wavelength of 470 nm results.

Comparative Example 2 cf. WO 2007/028159 A2, Example 2

9.74 g of Nanocryl D322 (50 wt. % of $SiO_2$, 20 nm particles, dispersed in urethane dimethacrylate (80 wt. %) and triethylene glycol dimethacrylate; Hanse Chemie), 0.01 g of camphorquinone, 0.05 g of EDAB (ethyl(4-N,N-dimethylamino)benzoate, Aldrich) and 0.2 g of Lucirin TPO (2,4,6-trimethylbenzoyldiphenylphosphine oxide; Aldrich) were blended at 50° C. A transparent composition which is photocurable by irradiation with light having a wavelength of 470 nm results.

Comparative Example 3 cf. WO 2007/028159 A2, Example 3

2.5 g of PENTA (dipentaerythritol pentaacrylate phosphoric acid ester), 1.8 g of Nanocryl XP21/0568 (50 wt. % of $SiO_2$, 20 nm particles, dispersed in triethylene glycol dimethacrylate; Hanse Chemie), 1.5 g of Nanocryl XP21/0746 (50 wt. % of $SiO_2$, 20 nm particles, dispersed in hydroxyethyl methacrylate; Hanse Chemie), 2.5 g of Nanocryl D322 (50 wt. % of $SiO_2$, 20 nm particles, dispersed in urethane dimethacrylate (80 wt. %) and triethylene glycol dimethacrylate; Hanse Chemie), 0.5 g of Nanocryl XP21/1045 (50 wt. % of $SiO_2$, 20 nm particles, dispersed in trimethylpropane triacrylate; Hanse Chemie), 1.0 g of bis-HEMA phosphate, 0.02 g of camphorquinone, 0.08 g of EDAB (ethyl (4-N,N-dimethylamino)benzoate; Aldrich) and 0.1 g of Lucirin TPO (2,4,6-trimethylbenzoyldiphenylphosphine oxide; Aldrich) were blended at 50° C. A transparent composition which is photocurable by irradiation with light having a wavelength of 470 nm results.

Example 17

Comparative Investigation of Physical and Mechanical Properties

The compositions prepared in Examples 3 to 16 and those prepared in Comparative Examples 1 to 3 (if necessary after curing and production of a suitable test specimen) were investigated according to the abovementioned methods for their adhesion, adhesion TC, flexural strength, flexural strength TC, abrasion, transmission, water uptake and flow properties (contact angle). The results determined are summarized in the following Table 1.

The comparison of the results according to Table 1 shows that the compositions according to the invention according to Examples 3 to 8 and 10 to 15, with a similar content of filler, are superior to the comparison compositions with respect to their mechanical properties. They have an excellent adhesion to tooth tissue, and at the same time they have decidedly good mechanical properties and very high transmissions. In this context, the compositions according to the invention have a low water uptake in the cured form and furthermore excellent flow properties.

A comparison of the results for Examples 3 to 8 with the result for Example 9 moreover shows, just as a comparison of the results for Examples 10 to 15 with the result for Example 16, that in spite of sometimes very high filler contents, in each case the transmission of the examples according to the invention does not deviate decisively from that of the comparison examples.

TABLE 1

Results for Example 17

| | Adhesion [MPa] | Adhesion TC [MPa] | Flexural strength [MPa] | Flexural strength TC [MPa] | Abrasion [μm] | Transmission [%] Vis. | Water uptake [μg/mm³] | Contact angle [°] |
|---|---|---|---|---|---|---|---|---|
| Comparative Example 1: | 12.5 | 10.8 | 71.3 | 65.3 | 92 | 85.0 | n.d. | n.d. |
| Comparative Example 2: | 13.1 | 8.9 | 78.3 | 71.6 | 88.7 | 86.1 | n.d. | n.d. |
| Comparative Example 3: | 17.9 | 13.2 | 61.5 | 53.2 | 111 | 85.9 | n.d. | n.d. |
| Example 3 | 12.4 | 9.8 | 95.6 | 94.3 | 143 | 89.3 | 17.9 | 31.4 |
| Example 4 | 13.9 | 8.4 | 98.4 | 95.4 | 111 | 88.7 | 16.4 | 33.1 |
| Example 5 | 15.2 | 9.3 | 101.3 | 98.7 | 88 | 88.7 | 16.0 | 33.7 |
| Example 6 | 17.8 | 13.5 | 105.8 | 97.6 | 65 | 88.4 | 14.2 | 34.9 |
| Example 7 | 20.2 | 18.9 | 111.6 | 107.8 | 58 | 87.5 | 13.5 | 35.7 |
| Example 8 | 19.5 | 19 | 125.3 | 118.9 | 53 | 87.3 | 12.2 | 37.3 |
| Example 9 (comparison) | 9.5 | 6.3 | 82.9 | 76.1 | 145 | 90.0 | 41.3 | 31.3 |
| Example 10 | 15.7 | 12.4 | 125.2 | 129.2 | 115.8 | 89.1 | 11.8 | 30.5 |
| Example 11 | 17.7 | 10.7 | 128.9 | 130.7 | 89.9 | 88.5 | 11.8 | 33.2 |
| Example 12 | 19.3 | 11.8 | 132.7 | 135.2 | 71.3 | 89.1 | 11.6 | 32.8 |
| Example 13 | 22.0 | 17.1 | 138.6 | 133.7 | 52.7 | 88.7 | 9.9 | 33.9 |
| Example 14 | 25.7 | 24.0 | 146.2 | 147.7 | 47.0 | 87.9 | 8.6 | 35.9 |
| Example 15 | 24.8 | 24.1 | 151.2 | 162.9 | 42.9 | 87.6 | 7.6 | 36.2 |
| Example 16 (comparison) | 12.1 | 8.0 | 108.6 | 104.3 | 117.5 | 90.1 | 13.5 | 29.3 | n.d. = not determined

Example 18

Comparison of the Transmissions of Test Specimens Based on Different Compositions at Various Wavelengths Test specimens were produced from compositions according to the invention prepared according to Examples 3 to 8 and 10 to 15 and from (comparison) compositions from Examples 9 and 16 and were investigated for their transmission at the wavelengths of 300, 400 and 500 nm according to the abovementioned methods for determination of the transmission at certain wavelengths. The results determined are summarized in the following Table 2.

The comparison of the results according to Table 2 shows that test specimens based on compositions according to the invention from Examples 3 to 8 already have excellent transmission properties, and the transmissions are far above 80%. By varying the constituent of the organic binder system in Examples 10 to 15 according to the invention, however, it was possible to improve the transmission values still further, above all at the short wavelengths of 300, 400 and 500 nm. Examples 9 (comparison) and 16 (comparison) relate to systems without a filler content and therefore of course show still better transmission values.

TABLE 2

Results for Example 18

| | Transmission 300 nm [%, 1 mm layer thickness] | Transmission 400 nm [%, 1 mm layer thickness] | Transmission 500 nm [%, 1 mm layer thickness] |
|---|---|---|---|
| Example 3 | 88.2 | 90.1 | 90.2 |
| Example 4 | 87.5 | 88.6 | 89.4 |
| Example 5 | 86.4 | 87.9 | 88.3 |
| Example 6 | 85.8 | 86.7 | 87.1 |
| Example 7 | 84.6 | 85.8 | 86.4 |
| Example 8 | 84.1 | 84.6 | 85.4 |
| Example 9 (comparison) | 90.1 | 90.1 | 90.1 |
| Example 10 | 92.4 | 94.1 | 94.7 |
| Example 11 | 91.7 | 93.0 | 94.1 |
| Example 12 | 91.1 | 92.5 | 91.8 |
| Example 13 | 89.8 | 91.0 | 91.7 |
| Example 14 | 87.9 | 90.0 | 90.9 |
| Example 15 | 87.9 | 88.9 | 89.7 |
| Example 16 (comparison) | 94.6 | 94.6 | 94.6 |

Example 19

Comparison of the Transmissions of Dry and Water-Stored Test Specimens Based on Compositions According to the Invention The test specimens investigated in Example 18 which were produced from the products according to Examples 7, 8, 14 and 15 were placed in water for one week, subsequently dabbed dry and measured again for their transmission. The results determined are summarized in the following Table 3.

The comparison of the transmissions of the test specimens which had not been stored in water (cf. Example 18, Table 2) with the transmissions of materials stored in water shows that the storage in water has a merely minimal effect on the transmission. Test specimens based on compositions according to the invention which contain both the monomer component (b1) and the monomer component (b2) (Examples 14 and 15) show a particularly low change in the transmission after storage in water.

TABLE 3

Results for Example 19 - Values after storage in water

| | Transmission 300 nm [%, 1 mm layer thickness] | Transmission 400 nm [%, 1 mm layer thickness] | Transmission 500 nm [%, 1 mm layer thickness] |
|---|---|---|---|
| Example 7 | 81.0 | 82.3 | 82.9 |
| Example 8 | 80.8 | 81.4 | 82.0 |
| Example 14 | 85.8 | 88.2 | 89.0 |
| Example 15 | 86.1 | 86.9 | 87.9 |

The invention claimed is:

1. A method for treatment of hard tooth tissue, comprising:
(A) infiltration and sealing of hard tooth tissue with a composition comprising:
   (a) a filler system comprising inorganic filler particles surface-modified by means of organic structural elements, wherein the organic structural elements is reactable with an organic binder system to form covalent bonds,
      wherein the filler particles of the composition have an average particle size in the range between 1 nm and 150 nm,
   (b) an organic binder system comprising one or more polymerizable monomers, wherein the filler system (a) is dispersed in the organic binder system (b), wherein step (A) comprises curing said composition; and
(B) detecting caries in the infiltrated region of the hard tooth tissue or under the seal of the hard tooth tissue by means of fluorescence, and/or
(C) determining changes in the condition of the seal of the hard tooth tissue by means of fluorescence, wherein step (B) and/or step (C) occur after step (A),
wherein the cured composition results in a sealing material which, at a layer thickness of 1 mm, has a transmission of 70% or more for perpendicularly incident radiation, wherein
(a) the transmission is determined in the entire wavelength spectrum of visual light, and/or
(b) the transmission is determined at a wavelength of 500 nm.

2. The method according to claim 1, wherein step (B) and/or step (C) comprise:
   irradiation of the infiltrated or sealed surface of the hard tooth tissue with excitation radiation which causes emission of fluorescence radiation,
   recording of the corresponding fluorescence radiation data.

3. The method according to claim 1, further comprising:
   comparing fluorescence radiation data recorded with reference data obtained from healthy teeth.

4. The method according to claim 1, wherein one, several, or all of the one or more polymerizable monomers comprise at least one structural element Z which independently of any further structural elements Z is chosen from the group consisting of
—O—(C=O)—CH=CH$_2$,   —O—(C=O)—C(CH$_3$)=CH$_2$,   —(C=O)—CH=CH$_2$,   —(C=O)—C(CH$_3$)=CH$_2$,   —CH=CH$_2$,   —C(CH$_3$)=CH$_2$ and —O—CH=CH$_2$.

5. The method according to claim 1, wherein the composition comprises no Bis-GMA.

6. The method according to claim 1, wherein the composition comprises no compound having a bisphenol A structural element.

7. The method according to claim 1, wherein one, several, or all of the one or more polymerizable monomers are polymerizable by means of free radicals or without free radicals.

8. The method according to claim 1, wherein the organic structural elements is reactable with the monomers, to form covalent bonds, by means of free radicals or without free radicals.

9. The method according to claim 1, wherein the cured composition to results in a sealing material which has a flexural strength of more than 80 MPa.

10. The method according to claim 1, wherein the cured composition results in a sealing material which has an abrasion of less than 80 μm after 200,000 cycles.

11. The method according to claim 1, wherein in alternative (a) the transmission is determined in the entire wavelength spectrum of visual light with a spectrocolorimeter; wherein in alternative (b) the transmission is determined with a UV/VIS spectrometer; or both.

12. The method according to claim 1, wherein a contact angle of the composition on dry tooth enamel, measured with a contact angle meter, is less than 60°.

13. The method according to claim 1, further comprising, curing the composition to give a sealing material which has a water uptake of less than 15 μm/mm$^3$.

14. The method according to claim 1, wherein the inorganic filler particles surface-modified by means of organic structural elements are chosen from the group of particles of silicon oxide, zirconium oxide, aluminium oxide and mixed oxides thereof surface-modified by means of organic structural elements.

15. The method according to claim 1, wherein the composition comprises no filler particles other than inorganic filler particles surface-modified by means of organic structural elements.

16. The method according to claim 1, comprising more than 40 wt. % of filler particles, based on the total weight of the composition.

17. The method according to claim 1, wherein the organic binder system comprises one or more additives which render possible or assist in (i) a photocuring and/or (ii) chemical curing of one, several, or all of the one or more polymerizable monomers.

18. The method according to claim 1, wherein the composition comprises in total less than 1.00 wt. %, based on the total weight of the composition, of initiators which (in particular in combination with accelerators) render possible (i) a photocuring and/or (ii) chemical curing of one, several, or all of the one or more polymerizable monomers.

19. The method according to claim 1, wherein the composition comprises no initiators which have phosphine oxide groups.

20. The method according to claim 1, wherein the composition comprises no compounds which have phosphine oxide groups.

21. The method according to claim 1, wherein the composition is prepared by the method comprising:
   (a) provision or preparation of a colloidal solution of inorganic particles in water,
   (b) exchange of the water for an organic solvent which is completely miscible with water,
   (c) before or after step (b), modification of the surface of the inorganic particles, so that particles which are surface-modified by means of organic structural elements result, it being possible for the organic structural elements to be reacted with the monomers to form covalent bonds, and (d) partial or complete exchange of the organic solvent which is completely miscible with water for the organic binder system comprising one, several, or all of the one or more polymerizable monomers.

22. The method according to claim 1, wherein the composition further comprises a fluorescent dyestuff.

23. A method for treatment of hard tooth tissue, comprising:
(A) infiltration and sealing of hard tooth tissue with a composition comprising:
  (a) a filler system comprising inorganic filler particles surface-modified by means of organic structural elements, wherein the organic structural elements is reactable with an organic binder system to form covalent bonds,
    wherein the filler particles of the composition have an average particle size in the range between 1 nm and 150 nm,
  (b) an organic binder system comprising one or more polymerizable monomers, wherein the filler system (a) is dispersed in the organic binder system (b), wherein step (a) comprises curing said composition; and
(B) detecting caries in the infiltrated region of the hard tooth tissue or under the seal of the hard tooth tissue by means of fluorescence, and/or
(C) determining changes in the seal of the hard tooth tissue by means of fluorescence, wherein step (B) and/or step (C) occur after step (A), wherein the total amount of the organic binder system (b) comprises
(b1) one, several, or all of the one or more polymerizable monomers chosen from the group consisting of compounds (monomers) the structure $Q(Y_xZ_e)_b$, wherein:
  Q denotes a saturated or olefinically unsaturated polyalicyclic structural element chosen from the group consisting of bicyclic, tricyclic, tetracyclic, pentacyclic and hexacyclic hydrocarbon radicals,
  b is a natural number chosen from the group of natural numbers 1, 2, 3 and 4,
  each Z denotes a structural element which independently of any further structural elements Z is chosen from the group consisting of
    —O—(C=O)—CH=CH$_2$, —O—(C=O)—C(CH$_3$)=CH$_2$,
    —(C=O)—CH=CH$_2$, —(C=O)—C(CH$_3$)=CH$_2$
    —CH=CH$_2$, —C(CH$_3$)=CH$_2$ and
    —O—CH=CH$_2$,
  each index e is a natural number which independently of any further indices e is chosen from the group of natural numbers 1, 2, 3 and 4,
  each index x denotes independently of any further indices x 0 or 1,
  each Y denotes in the structure $Q(Y_xZ_e)_b$ where x=1 a structural element which bonds the polyalicyclic structural element Q to e structural elements Z, wherein each Y is chosen independently of any further structural elements Y,
and/or
(b2) one, several, or all of the one or more polymerizable monomers, wherein the polymerizable monomer or monomers is or are not compounds (monomers) of the structure $Q(Y_xZ_e)_b$ defined above.

24. The method according to claim 23, wherein the structural element Q of the compounds of the structure $Q(Y_xZ_e)_b$ of component (b1) denotes a tricyclo[5.2.1.0$^{2,6}$]decane radical, a tricyclo[5.2.1.0$^{2,6}$]dec-3-ene radical, a tricyclo [3.3.1.1$^{3,7}$]decane radical or a[2.2.1]heptane radical.

25. The method according to claim 23, characterized in that one, two or more compounds of the structure $Q(Y_xZ_e)_b$ of the monomer component (b1) have a tricyclo[5.2.1.0$^{2,6}$]-decane or tricyclo[5.2.1.0$^{2,6}$]-decene structural element.

26. The method according to claim 23, wherein Z is chosen from the group consisting of —O—(C=O)—CH=CH$_2$ and —O—(C=O)—C(CH$_3$)=CH$_2$.

27. The method according to claim 23, wherein component (bit) comprises or consists of bis(methacryloyloxymethyl)-tricyclo[5.2.1.0$^{2,6}$]decane and/or bis(acryloyloxymethyl)tricyclo[5.2.1.0$^{2,6}$]decane.

28. The method according to claim 23, wherein one, several, or all of the one or more polymerizable monomers of the monomer component (b2) is or are chosen from the group consisting of acrylates and methacrylates.

29. The method according to claim 23, wherein one, several, or all of the one or more polymerizable monomers of the monomer component (b2) is or are chosen from the group consisting of triethylene glycol dimethacrylate (TEDMA), urethane dimethacrylate (7,7,9-trimethyl-4,13-dioxo-3,14-dioxa-5,12-diazahexadecane 1,16-dioxydimethacrylate (UDMA)), glycerol dimethacrylate (GlyDMA) and bisphenol A glycidyl methacrylate (Bis-GMA).

30. The method according to claim 23, wherein the ratio of the total weight of component (hi) to the total weight of component (b2) is in the range of from 4:1 to 1:3.

31. The method according to claim 23, wherein the organic structural elements is reactable with the monomers, to form covalent bonds, by means of free radicals or without free radicals, with one or more monomers of components (b1) and/or (b2).

32. The method according to claim 23, wherein one, two or more of the hydrogen atoms of polyalicyclic structural element Q that are not substituted by substituents $Y_xZ_e$ are substituted by alkyl groups, alkoxy groups, halogen atoms or trifluoromethyl groups.

* * * * *

UNITED STATES PATENT AND TRADEMARK OFFICE
CERTIFICATE OF CORRECTION

PATENT NO. : 8,979,535 B2  
APPLICATION NO. : 13/645121  
DATED : March 17, 2015  
INVENTOR(S) : Plaumann et al.

Page 1 of 1

It is certified that error appears in the above-identified patent and that said Letters Patent is hereby corrected as shown below:

In the Claims

In Column 72, line 24 of Claim 27 reads "(bit) comprises or consists of ...."

but should read "(b1) comprises or consists of ...."

In Column 72, line 40 of Claim 30 reads "the total weight of component (hi) to the total weight of"

but should read "the total weight of component (b1) to the total weight of"

Signed and Sealed this
Twenty-seventh Day of October, 2015

Michelle K. Lee
*Director of the United States Patent and Trademark Office*